United States Patent
Abe et al.

(10) Patent No.: US 9,353,153 B2
(45) Date of Patent: May 31, 2016

(54) CYCLIC RNA AND PROTEIN PRODUCTION METHOD

(71) Applicant: RIKEN, Saitama (JP)

(72) Inventors: Hiroshi Abe, Sapporo (JP); Naoko Abe, Sapporo (JP); Yoshihiro Ito, Tokyo (JP); Mizuki Nishihara, Tokyo (JP)

(73) Assignee: RIKEN (JP)

( * ) Notice: Subject to any disclaimer, the term of this patent is extended or adjusted under 35 U.S.C. 154(b) by 0 days.

(21) Appl. No.: 14/376,665

(22) PCT Filed: Feb. 8, 2013

(86) PCT No.: PCT/JP2013/053095
§ 371 (c)(1),
(2) Date: Aug. 5, 2014

(87) PCT Pub. No.: WO2013/118878
PCT Pub. Date: Aug. 15, 2013

(65) Prior Publication Data
US 2015/0079630 A1    Mar. 19, 2015

(30) Foreign Application Priority Data
Feb. 9, 2012 (JP) ................................. 2012-026506

(51) Int. Cl.
| | |
|---|---|
| *C12P 21/00* | (2006.01) |
| *C12P 21/02* | (2006.01) |
| *C07K 7/06* | (2006.01) |
| *C12N 15/10* | (2006.01) |
| *C12N 15/66* | (2006.01) |
| *C12N 15/67* | (2006.01) |
| *C12N 15/70* | (2006.01) |
| *C12N 15/79* | (2006.01) |
| *C12N 15/00* | (2006.01) |

(52) U.S. Cl.
CPC . *C07K 7/06* (2013.01); *C12N 15/10* (2013.01); *C12N 15/66* (2013.01); *C12P 21/00* (2013.01); *C12P 21/02* (2013.01)

(58) Field of Classification Search
None
See application file for complete search history.

(56) References Cited

FOREIGN PATENT DOCUMENTS

| | | |
|---|---|---|
| WO | WO 97/07825 A1 | 3/1997 |
| WO | WO 03/002713 A2 | 1/2003 |
| WO | WO 2010/037835 A2 | 4/2010 |
| WO | WO 2010/038155 A2 | 4/2010 |

OTHER PUBLICATIONS

Surono et al. "Circular dystrophin RNAs consisting of exons that were skipped by alternative splicing" 8(3) Human Molecular Genetics 493-500 (1999).*
Kozak et al., "Point mutations define a sequence flanking the AUG initiatior codon that modulates translation by eukaryotic ribosomes" 44(2) Cell 283-292 (1986).*
International Search Report and Written Opinion mailed Mar. 12, 2013 in corresponding PCT International Application No. PCT/JP2013/053095.
R. Perriman et al., "Circular mRNA can direct translation of extremely long repeating-sequence proteins in vivo," RNA (1998), vol. 4, pp. 1047-1054.
C. Chen et al., "Initiation of Protein Synthesis by the Eukaryotic Translational Apparatus of Circular RNAs," Science (1995), vol. 268, pp. 415-417.
Chen et al., "Initiation of Protein Synthesis by the Eukaryotic Translational Apparatus on Circular RNAs", Science, vol. 268, Apr. 21, 1995, pp. 415-417.

* cited by examiner

*Primary Examiner* — Nancy J Leith
(74) *Attorney, Agent, or Firm* — Ostrolenk Faber LLP

(57) ABSTRACT

The present invention provides a cyclic RNA preferable for carrying out rotary protein translation in which translation domains other than that of the target protein are sufficiently short and translation efficiency is high, and a method for producing protein that uses this cyclic RNA as template. More specifically, the present invention provides a cyclic RNA that encodes a protein, has a full-length number of bases that is equal to or greater than 102 and is a multiple of 3, has at least one start codon, does not have a stop codon in the same reading frame as the start codon, and does not contain an internal ribosome entry site (IRES). In addition, the present invention provides a method for producing protein in a eukaryotic cell expression system that consists of using the aforementioned cyclic RNA as template and expressing a protein encoded by that cyclic RNA.

15 Claims, 10 Drawing Sheets

SEQUENCE LISTING

```
<160> NUMBER OF SEQ ID NOS: 49

<210> SEQ ID NO 1
<211> LENGTH: 35
<212> TYPE: RNA
<213> ORGANISM: Artificial Sequence
<220> FEATURE:
<223> OTHER INFORMATION: F35

<400> SEQUENCE: 1
auuauuaagg agauauaucc gaugauuauu gacua                              35

<210> SEQ ID NO 2
<211> LENGTH: 49
<212> TYPE: RNA
<213> ORGANISM: Artificial Sequence
<220> FEATURE:
<223> OTHER INFORMATION: F49

<400> SEQUENCE: 2
caaggacgac gaugacaaaa uuauugacua caaggacgac gaugacaaa              49

<210> SEQ ID NO 3
<211> LENGTH: 42
<212> TYPE: RNA
<213> ORGANISM: Artificial Sequence
<220> FEATURE:
<223> OTHER INFORMATION: F42

<400> SEQUENCE: 3
cugcugauua uugacuacaa ggacgacgau gacaaaauua uu                     42

<210> SEQ ID NO 4
<211> LENGTH: 48
<212> TYPE: RNA
<213> ORGANISM: Artificial Sequence
<220> FEATURE:
<223> OTHER INFORMATION: F42'

<400> SEQUENCE: 4
cugcugauua uugacuacaa ggacgacgau gacaaaauua uuuaauaa               48

<210> SEQ ID NO 5
<211> LENGTH: 20
<212> TYPE: DNA
<213> ORGANISM: Artificial Sequence
<220> FEATURE:
```

```
<223> OTHER INFORMATION: G1

<400> SEQUENCE: 5
tcgtccttgt agtcaataat                                                    20

<210> SEQ ID NO 6
<211> LENGTH: 18
<212> TYPE: DNA
<213> ORGANISM: Artificial Sequence
<220> FEATURE:
<223> OTHER INFORMATION: G2

<400> SEQUENCE: 6
aatcagcagt ttgtcatc                                                      18

<210> SEQ ID NO 7
<211> LENGTH: 24
<212> TYPE: DNA
<213> ORGANISM: Artificial Sequence
<220> FEATURE:
<223> OTHER INFORMATION: G3

<400> SEQUENCE: 7
ctccttaata ataataattt tgtc                                               24

<210> SEQ ID NO 8
<211> LENGTH: 24
<212> TYPE: DNA
<213> ORGANISM: Artificial Sequence
<220> FEATURE:
<223> OTHER INFORMATION: G3'

<400> SEQUENCE: 8
ctccttaata atttattaaa taat                                               24

<210> SEQ ID NO 9
<211> LENGTH: 20
<212> TYPE: DNA
<213> ORGANISM: Artificial Sequence
<220> FEATURE:
<223> OTHER INFORMATION: G4

<400> SEQUENCE: 9
ccttaataat tttgtcatcg                                                    20

<210> SEQ ID NO 10
<211> LENGTH: 84
<212> TYPE: RNA
<213> ORGANISM: Artificial Sequence
<220> FEATURE:
<223> OTHER INFORMATION: C84

<400> SEQUENCE: 10
auuauuaagg agauauaucc gaugauuauu gacuacaagg acgacgauga caaaauuauu         60
gacuacaagg acgacgauga caaa                                               84

<210> SEQ ID NO 11
<211> LENGTH: 126
<212> TYPE: RNA
<213> ORGANISM: Artificial Sequence
<220> FEATURE:
<223> OTHER INFORMATION: C126

<400> SEQUENCE: 11
auuauuaagg agauauaucc gaugauuauu gacuacaagg acgacgauga caaaauuauu         60
```

```
gacuacaagg acgacgauga caaacugcug auuauugacu acaaggacga cgaugacaaa    120
auuauu                                                                126

<210> SEQ ID NO 12
<211> LENGTH: 126
<212> TYPE: RNA
<213> ORGANISM: Artificial Sequence
<220> FEATURE:
<223> OTHER INFORMATION: C126+stop

<400> SEQUENCE: 12
auuauuaagg agauauaucc gaugauuauu gacuacaagg acgacgauga caaaauuauu    60
gacuacaagg acgacgauga caaacugcug auuauugacu acaaggacga cgaugacaaa   120
auuauu                                                               126

<210> SEQ ID NO 13
<211> LENGTH: 168
<212> TYPE: RNA
<213> ORGANISM: Artificial Sequence
<220> FEATURE:
<223> OTHER INFORMATION: C168

<400> SEQUENCE: 13
auuauuaagg agauauaucc gaugauuauu gacuacaagg acgacgauga caaaauuauu    60
gacuacaagg acgacgauga caaaauuauu aaggagauau auccgaugau uauugacuac   120
aaggacgacg augacaaaau uauugacuac aaggacgacg augacaaa                 168

<210> SEQ ID NO 14
<211> LENGTH: 252
<212> TYPE: RNA
<213> ORGANISM: Artificial Sequence
<220> FEATURE:
<223> OTHER INFORMATION: C252

<400> SEQUENCE: 14
auuauuaagg agauauaucc gaugauuauu gacuacaagg acgacgauga caaaauuauu    60
gacuacaagg acgacgauga caaacugcug auuauugacu acaaggacga cgaugacaaa   120
auuauuauua uuaaggagau auaccgaug auuauugacu acaaggacga cgaugacaaa    180
auuauugacu acaaggacga cgaugacaaa cugcugauua uugacuacaa ggacgacgau   240
gacaaaauua uu                                                        252

<210> SEQ ID NO 15
<211> LENGTH: 155
<212> TYPE: DNA
<213> ORGANISM: Artificial Sequence
<220> FEATURE:
<223> OTHER INFORMATION: Fragmnent 1

<400> SEQUENCE: 15
actttatcgt cgtcgtcttt atagtcaatt atcttgtcgt cgtcgtcctt gtagtcgatg    60
atcttgtcgt cgtcgtcctt gtagtcgatg atcttgtcgt cgtcgtcctt gtagtccatg   120
gtggctccct atagtgagtc gtattaggat ccgcg                               155

<210> SEQ ID NO 16
<211> LENGTH: 129
<212> TYPE: DNA
<213> ORGANISM: Artificial Sequence
<220> FEATURE:
```

<223> OTHER INFORMATION: Fragment 2

<400> SEQUENCE: 16

```
atctggttga atttatcgtc gtcgtctttg tagtctataa tcttgtcgtc gtcgtccttg    60
tagtcgatga tcttgtcgtc gtcgtccttg tagtcgatga tcttgtcgtc gtcgtcttta   120
tagtccagt                                                           129
```

<210> SEQ ID NO 17
<211> LENGTH: 129
<212> TYPE: DNA
<213> ORGANISM: Artificial Sequence
<220> FEATURE:
<223> OTHER INFORMATION: Fragment 3

<400> SEQUENCE: 17

```
cctctagagg gtttatcgtc gtcgtccttg taatctatta tcttgtcgtc gtcgtccttg    60
tagtcgatga tcttgtcgtc gtcgtccttg tagtcgatga tcttgtcgtc gtcgtcctta   120
taatcggat                                                           129
```

<210> SEQ ID NO 18
<211> LENGTH: 20
<212> TYPE: DNA
<213> ORGANISM: Artificial Sequence
<220> FEATURE:
<223> OTHER INFORMATION: Adaptor 1 (for 4x FLAG RNA)

<400> SEQUENCE: 18

```
ggtggctccc actttatcgt                                                20
```

<210> SEQ ID NO 19
<211> LENGTH: 20
<212> TYPE: DNA
<213> ORGANISM: Artificial Sequence
<220> FEATURE:
<223> OTHER INFORMATION: Adaptor 2 (for 8x FLAG RNA)

<400> SEQUENCE: 19

```
ggtggctccc atctggttga                                                20
```

<210> SEQ ID NO 20
<211> LENGTH: 20
<212> TYPE: DNA
<213> ORGANISM: Artificial Sequence
<220> FEATURE:
<223> OTHER INFORMATION: Adaptor 3 (for 12x FLAG RNA)

<400> SEQUENCE: 20

```
ggtggctccc cctctagagg                                                20
```

<210> SEQ ID NO 21
<211> LENGTH: 40
<212> TYPE: DNA
<213> ORGANISM: Artificial Sequence
<220> FEATURE:
<223> OTHER INFORMATION: Forward Primer 1

<400> SEQUENCE: 21

```
cgcggatcct aatacgactc actataggga gccaccatgg                          40
```

<210> SEQ ID NO 22
<211> LENGTH: 20
<212> TYPE: DNA
<213> ORGANISM: Artificial Sequence

```
<220> FEATURE:
<223> OTHER INFORMATION: Adaptor oligo 1

<400> SEQUENCE: 22
acgataaagt actggactat                                              20

<210> SEQ ID NO 23
<211> LENGTH: 20
<212> TYPE: DNA
<213> ORGANISM: Artificial Sequence
<220> FEATURE:
<223> OTHER INFORMATION: Adaptor oligo 2

<400> SEQUENCE: 23
tcaaccagat atccgattat                                              20

<210> SEQ ID NO 24
<211> LENGTH: 15
<212> TYPE: DNA
<213> ORGANISM: Artificial Sequence
<220> FEATURE:
<223> OTHER INFORMATION: Reverse primer 1

<400> SEQUENCE: 24
cctctagagg gttta                                                   15

<210> SEQ ID NO 25
<211> LENGTH: 15
<212> TYPE: DNA
<213> ORGANISM: Artificial Sequence
<220> FEATURE:
<223> OTHER INFORMATION: Reverse primer 2

<400> SEQUENCE: 25
atctggttga attta                                                   15

<210> SEQ ID NO 26
<211> LENGTH: 155
<212> TYPE: DNA
<213> ORGANISM: Artificial Sequence
<220> FEATURE:
<223> OTHER INFORMATION: Fragment 1 DNA sense

<400> SEQUENCE: 26
cgcggatcct aatacgactc actataggga gccaccatgg actacaagga cgacgacgac    60
aagatcatcg actacaagga cgacgacgac aagatcatcg actacaagga cgacgacgac   120
aagataattg actataaaga cgacgacgat aaagt                              155

<210> SEQ ID NO 27
<211> LENGTH: 17
<212> TYPE: DNA
<213> ORGANISM: Artificial Sequence
<220> FEATURE:
<223> OTHER INFORMATION: Reverse primer 3

<400> SEQUENCE: 27
ttctggttga atttatc                                                 17

<210> SEQ ID NO 28
<211> LENGTH: 17
<212> TYPE: DNA
<213> ORGANISM: Artificial Sequence
<220> FEATURE:
<223> OTHER INFORMATION: Revserse primer 4
```

```
<400> SEQUENCE: 28
tttcagttga atttatc                                              17

<210> SEQ ID NO 29
<211> LENGTH: 20
<212> TYPE: DNA
<213> ORGANISM: Artificial Sequence
<220> FEATURE:
<223> OTHER INFORMATION: Adaptor 4 (for 8x FLAG (2) RNA)

<400> SEQUENCE: 29
ggtggctccc ttctggttga                                           20

<210> SEQ ID NO 30
<211> LENGTH: 20
<212> TYPE: DNA
<213> ORGANISM: Artificial Sequence
<220> FEATURE:
<223> OTHER INFORMATION: Adaptor 5 (for 8x FLAG (stop) RNA)

<400> SEQUENCE: 30
ggtggctccc tttcagttga                                           20

<210> SEQ ID NO 31
<211> LENGTH: 23
<212> TYPE: DNA
<213> ORGANISM: Artificial Sequence
<220> FEATURE:
<223> OTHER INFORMATION: Reverse primer 5

<400> SEQUENCE: 31
tcttcctttc cgttgaattt atc                                       23

<210> SEQ ID NO 32
<211> LENGTH: 23
<212> TYPE: DNA
<213> ORGANISM: Artificial Sequence
<220> FEATURE:
<223> OTHER INFORMATION: Reverse primer 6

<400> SEQUENCE: 32
tcttactatc agttgaattt atc                                       23

<210> SEQ ID NO 33
<211> LENGTH: 20
<212> TYPE: DNA
<213> ORGANISM: Artificial Sequence
<220> FEATURE:
<223> OTHER INFORMATION: Adaptor 6 (for 8x FLAG (3) circular RNA)

<400> SEQUENCE: 33
ggtggctccc tcttcctttc                                           20

<210> SEQ ID NO 34
<211> LENGTH: 20
<212> TYPE: DNA
<213> ORGANISM: Artificial Sequence
<220> FEATURE:
<223> OTHER INFORMATION: Adaptor 7 (for 8x FLAG (3 stop) circular RNA)

<400> SEQUENCE: 34
ggtggctccc tcttactatc                                           20

<210> SEQ ID NO 35
<211> LENGTH: 20
```

```
<212> TYPE: DNA
<213> ORGANISM: Artificial Sequence
<220> FEATURE:
<223> OTHER INFORMATION: Forward primer 2

<400> SEQUENCE: 35
cgcggatcct aatacgactc                                                 20

<210> SEQ ID NO 36
<211> LENGTH: 155
<212> TYPE: DNA
<213> ORGANISM: Artificial Sequence
<220> FEATURE:
<223> OTHER INFORMATION: 4x FLAG DNA

<400> SEQUENCE: 36
cgcggatcct aatacgactc actatagggga gccaccatgg actacaagga cgacgacgac    60
aagatcatcg actacaagga cgacgacgac aagatcatcg actacaagga cgacgacgac   120
aagataattg actataaaga cgacgacgat aaagt                              155

<210> SEQ ID NO 37
<211> LENGTH: 284
<212> TYPE: DNA
<213> ORGANISM: Artificial Sequence
<220> FEATURE:
<223> OTHER INFORMATION: 8x FLAG DNA

<400> SEQUENCE: 37
cgcggatcct aatacgactc actatagggga gccaccatgg actacaagga cgacgacgac    60
aagatcatcg actacaagga cgacgacgac aagatcatcg actacaagga cgacgacgac   120
aagataattg actataaaga cgacgacgat aaagtactgg actataaaga cgacgacgac   180
aagatcatcg actacaagga cgacgacgac aagatcatcg actacaagga cgacgacgac   240
aagattatag actacaaaga cgacgacgat aaattcaacc agat                    284

<210> SEQ ID NO 38
<211> LENGTH: 413
<212> TYPE: DNA
<213> ORGANISM: Artificial Sequence
<220> FEATURE:
<223> OTHER INFORMATION: 12x FLAG DNA

<400> SEQUENCE: 38
cgcggatcct aatacgactc actatagggga gccaccatgg actacaagga cgacgacgac    60
aagatcatcg actacaagga cgacgacgac aagatcatcg actacaagga cgacgacgac   120
aagataattg actataaaga cgacgacgat aaagtactgg actataaaga cgacgacgac   180
aagatcatcg actacaagga cgacgacgac aagatcatcg actacaagga cgacgacgac   240
aagattatag actacaaaga cgacgacgat aaattcaacc agatatccga ttataaggac   300
gacgacgaca agatcatcga ctacaaggac gacgacgaca agatcatcga ctacaaggac   360
gacgacgaca agataataga ttacaaggac gacgacgata aaccctctag agg          413

<210> SEQ ID NO 39
<211> LENGTH: 284
<212> TYPE: DNA
<213> ORGANISM: Artificial Sequence
<220> FEATURE:
<223> OTHER INFORMATION: 8x FLAG (2) DNA

<400> SEQUENCE: 39
```

```
cgcggatcct aatacgactc actatagggca gccaccatgg actacaagga cgacgacgac    60
aagatcatcg actacaagga cgacgacgac aagatcatcg actacaagga cgacgacgac   120
aagataattg actataaaga cgacgacgat aaagtactgg actataaaga cgacgacgac   180
aagatcatcg actacaagga cgacgacgac aagatcatcg actacaagga cgacgacgac   240
aagattatag actacaaaga cgacgacgat aaattcaacc agaa                    284
```

<210> SEQ ID NO 40
<211> LENGTH: 284
<212> TYPE: DNA
<213> ORGANISM: Artificial Sequence
<220> FEATURE:
<223> OTHER INFORMATION: 8x FLAG (stop) DNA

<400> SEQUENCE: 40

```
cgcggatcct aatacgactc actatagggca gccaccatgg actacaagga cgacgacgac    60
aagatcatcg actacaagga cgacgacgac aagatcatcg actacaagga cgacgacgac   120
aagataattg actataaaga cgacgacgat aaagtactgg actataaaga cgacgacgac   180
aagatcatcg actacaagga cgacgacgac aagatcatcg actacaagga cgacgacgac   240
aagattatag actacaaaga cgacgacgat aaattcaact gaaa                    284
```

<210> SEQ ID NO 41
<211> LENGTH: 290
<212> TYPE: DNA
<213> ORGANISM: Artificial Sequence
<220> FEATURE:
<223> OTHER INFORMATION: 8x FLAG (3) DNA

<400> SEQUENCE: 41

```
cgcggatcct aatacgactc actatagggca gccaccatgg actacaagga cgacgacgac    60
aagatcatcg actacaagga cgacgacgac aagatcatcg actacaagga cgacgacgac   120
aagataattg actataaaga cgacgacgat aaagtactgg actataaaga cgacgacgac   180
aagatcatcg actacaagga cgacgacgac aagatcatcg actacaagga cgacgacgac   240
aagattatag actacaaaga cgacgacgat aaattcaacg gaaaggaaga              290
```

<210> SEQ ID NO 42
<211> LENGTH: 290
<212> TYPE: DNA
<213> ORGANISM: Artificial Sequence
<220> FEATURE:
<223> OTHER INFORMATION: 8x FLAG (3 stop) DNA

<400> SEQUENCE: 42

```
cgcggatcct aatacgactc actatagggca gccaccatgg actacaagga cgacgacgac    60
aagatcatcg actacaagga cgacgacgac aagatcatcg actacaagga cgacgacgac   120
aagataattg actataaaga cgacgacgat aaagtactgg actataaaga cgacgacgac   180
aagatcatcg actacaagga cgacgacgac aagatcatcg actacaagga cgacgacgac   240
aagattatag actacaaaga cgacgacgat aaattcaact gatagtaaga              290
```

<210> SEQ ID NO 43
<211> LENGTH: 129
<212> TYPE: RNA
<213> ORGANISM: Artificial Sequence
<220> FEATURE:
<223> OTHER INFORMATION: 4x FLAG RNA

<400> SEQUENCE: 43
gggagccacc auggacuaca aggacgacga cgacaagauc aucgacuaca aggacgacga    60
cgacaagauc aucgacuaca aggacgacga cgacaagaua auugacuaua aagacgacga   120
cgauaaagu                                                          129

<210> SEQ ID NO 44
<211> LENGTH: 258
<212> TYPE: RNA
<213> ORGANISM: Artificial Sequence
<220> FEATURE:
<223> OTHER INFORMATION: 8x FLAG RNA

<400> SEQUENCE: 44
gggagccacc auggacuaca aggacgacga cgacaagauc aucgacuaca aggacgacga    60
cgacaagauc aucgacuaca aggacgacga cgacaagaua auugacuaua aagacgacga   120
cgauaaagua cuggacuaua aagacgacga cgacaagauc aucgacuaca aggacgacga   180
cgacaagauc aucgacuaca aggacgacga cgacaagauu auagacuaca aagacgacga   240
cgauaaauuc aaccagau                                                258

<210> SEQ ID NO 45
<211> LENGTH: 387
<212> TYPE: RNA
<213> ORGANISM: Artificial Sequence
<220> FEATURE:
<223> OTHER INFORMATION: 12x FLAG RNA

<400> SEQUENCE: 45
gggagccacc auggacuaca aggacgacga cgacaagauc aucgacuaca aggacgacga    60
cgacaagauc aucgacuaca aggacgacga cgacaagaua auugacuaua aagacgacga   120
cgauaaagua cuggacuaua aagacgacga cgacaagauc aucgacuaca aggacgacga   180
cgacaagauc aucgacuaca aggacgacga cgacaagauu auagacuaca aagacgacga   240
cgauaaauuc aaccagauau ccgauuauaa ggacgacgac gacaagauca ucgacuacaa   300
ggacgacgac gacaagauca ucgacuacaa ggacgacgac gacaagauaa uagauuacaa   360
ggacgacgac gauaaacccu cuagagg                                      387

<210> SEQ ID NO 46
<211> LENGTH: 258
<212> TYPE: RNA
<213> ORGANISM: Artificial Sequence
<220> FEATURE:
<223> OTHER INFORMATION: 8x FLAG (2) RNA

<400> SEQUENCE: 46
gggagccacc auggacuaca aggacgacga cgacaagauc aucgacuaca aggacgacga    60
cgacaagauc aucgacuaca aggacgacga cgacaagaua auugacuaua aagacgacga   120
cgauaaagua cuggacuaua aagacgacga cgacaagauc aucgacuaca aggacgacga   180
cgacaagauc aucgacuaca aggacgacga cgacaagauu auagacuaca aagacgacga   240
cgauaaauuc aaccagaa                                                258

<210> SEQ ID NO 47
<211> LENGTH: 258
<212> TYPE: RNA
<213> ORGANISM: Artificial Sequence
<220> FEATURE:
<223> OTHER INFORMATION: 8x FLAG (stop) RNA

```
<400> SEQUENCE: 47
gggagccacc auggacuaca aggacgacga cgacaagauc aucgacuaca aggacgacga        60
cgacaagauc aucgacuaca aggacgacga cgacaagaua auugacuaua aagacgacga       120
cgauaaagua cuggacuaua aagacgacga cgacaagauc aucgacuaca aggacgacga       180
cgacaagauc aucgacuaca aggacgacga cgacaagauu auagacuaca aagacgacga       240
cgauaaauuc aacugaaa                                                     258

<210> SEQ ID NO 48
<211> LENGTH: 264
<212> TYPE: RNA
<213> ORGANISM: Artificial Sequence
<220> FEATURE:
<223> OTHER INFORMATION: 8x FLAG (3) RNA

<400> SEQUENCE: 48
gggagccacc auggacuaca aggacgacga cgacaagauc aucgacuaca aggacgacga        60
cgacaagauc aucgacuaca aggacgacga cgacaagaua auugacuaua aagacgacga       120
cgauaaagua cuggacuaua aagacgacga cgacaagauc aucgacuaca aggacgacga       180
cgacaagauc aucgacuaca aggacgacga cgacaagauu auagacuaca aagacgacga       240
cgauaaauuc aacggaaagg aaga                                              264

<210> SEQ ID NO 49
<211> LENGTH: 264
<212> TYPE: RNA
<213> ORGANISM: Artificial Sequence
<220> FEATURE:
<223> OTHER INFORMATION: 8x FLAG (3 stop) RNA

<400> SEQUENCE: 49
gggagccacc auggacuaca aggacgacga cgacaagauc aucgacuaca aggacgacga        60
cgacaagauc aucgacuaca aggacgacga cgacaagaua auugacuaua aagacgacga       120
cgauaaagua cuggacuaua aagacgacga cgacaagauc aucgacuaca aggacgacga       180
cgacaagauc aucgacuaca aggacgacga cgacaagauu auagacuaca aagacgacga       240
cgauaaauuc aacugauagu aaga                                              264
```

CYCLIC RNA AND PROTEIN PRODUCTION METHOD

TECHNICAL FIELD

The present invention relates to a method for producing long-chain protein having a repetitive sequence by carrying out rotary protein translation using cyclic RNA, and to cyclic RNA used in that method.

BACKGROUND ART

Proteins having repetitive sequences (protein repeats) of theoretically infinite length can be synthesized by carrying out rotary protein translation using cyclic RNA not having a stop codon as template (a method of synthesizing a protein having an endless peptide repeat structure (also referred to as rolling circle translation). In the case of ordinary translation systems, the rate-limiting step of protein synthesis is initiation of peptide elongation after ribosomes have recognized and bound RNA.

For example, protein repeats are synthesized in Non-Patent Document 1 by a translation reaction of cyclic RNA using an *Escherichia coli* cell-free translation system. More specifically, rotary protein synthesis is carried out by using cyclic RNA, in which the protein open reading frame (ORF) is arranged downstream from a sequence consisting of a Shine-Dalgarno (SD) sequence, start codon (AUG) and downstream box (DB), as template.

In eukaryotic cell translation systems, the translation reaction is initiated by ribosomes recognizing and binding a complex formed at the start of the translation reaction by various translation factors binding to a cap structure on the 5'-terminal of mRNA and to a poly A chain on the 3'-terminal. Consequently, in the case of using cyclic RNA not having a cap structure or poly A chain as template, ribosome binding sites (structures able to be recognized and bound by ribosomes) are thought to be required that are capable of functioning in place of these structures. Therefore, in Non-Patent Document 2 and Patent Document 1, for example, cyclic RNA is used as template in which an internal ribosome entry site (IRES) derived from a virus (EMCV) is arranged upstream from the start codon in a rotary protein translation system that uses a cell-free translation system derived from rabbit reticulocytes.

PRIOR ART DOCUMENTS

Patent Documents

[Patent Document 1] International Publication No. WO 1997/07825

Non-Patent Documents

[Non-Patent Document 1] Perriman, R. and Ares, M., RNA (1998), Vol. 4, pp. 1047-1054
[Non-Patent Document 2] Sarnow, P. and Chen, C., Science (1995), Vol. 268, pp. 415-417

DISCLOSURE OF THE INVENTION

Problems to be Solved by the Invention

In the method described in Non-Patent Document 1, although a protein repeat (polyGFP) of green fluorescent protein (GFP) is synthesized, further improvement is required since translation efficiency is worse than that of the linear RNA prior to cyclization. In addition, since cyclic RNA is prepared using a splicing reaction, there is also the problem of the synthesis of the cyclic RNA per se being extremely complex. Moreover, this method is only realized in cells of *Escherichia coli* and there are no examples of application in animal cells.

On the other hand, in the method described in Non-Patent Document 2 and Patent Document 1, since the cyclic RNA serving as template has an IRES of a length of about 500 bases, in addition to the size of the cyclic RNA ending up becoming large, since the IRES domain is also translated, there is the problem of the generation of protein translation products other than the desired translation product. In addition, since there are also concerns over problems with safety, there is the problem of cyclic RNA containing an IRES sequence being unsuitable for medical applications. Moreover, similar to the method described in Non-Patent Document 1, this method is only realized in cell-free translation systems, and there are no descriptions of examples of application in animal cells.

An object of the present invention is to provide a cyclic RNA preferable for carrying out rotary protein translation in which translation domains other than that of the target protein are sufficiently short and translation efficiency is high, and a method for producing protein that uses this cyclic RNA as template.

Means for Solving the Problems

As a result of conducting extensive studies to solve the aforementioned problems, the inventors of the present invention found that by making the base length of cyclic RNA used as template in rotary protein translation to be within a specific range, translation efficiency can be dramatically improved, and even in the case of using cyclic RNA not having an IRES in a eukaryotic cell translation system, long-chain proteins having a target repetitive sequence can be synthesized, thereby leading to completion of the present invention.

Namely, the cyclic RNA and protein production method of the present invention adopt the configurations of [1] to [8] below.

[1] A cyclic RNA that encodes a protein, has a full-length number of bases that is equal to or greater than 102 and is a multiple of 3, has at least one start codon, does not have a stop codon in the same reading frame as the start codon, and does not contain an internal ribosome entry site (IRES).

[2] The cyclic RNA described in [1] above, wherein the full-length number of bases is 561 or less.

[3] The cyclic RNA described in [1] or [2] above, which has a Kozak sequence upstream from the start codon.

[4] A method for producing protein in a eukaryotic cell expression system, comprising:
expressing a protein encoded by the cyclic RNA using the cyclic RNA described in any of [1] to [3] above as template.

[5] The method for producing protein described in [4] above, wherein protein encoded by the cyclic RNA described in any of [1] to [3] above is expressed by
introducing the cyclic RNA described in any of [1] to [3] above into eukaryotic cells, or
adding the cyclic RNA described in any of [1] to [3] above to a cell-free expression system derived from eukaryotic cells.

[6] The method for producing protein described in [4] or [5] above, wherein the eukaryotic cells are mammalian cells.

[7] A cyclic RNA that encodes a protein, has a full-length number of bases that is from 102 to 360 and is a multiple of 3, has at least one IRES and one start codon within 1 to 20 bases downstream from the IRES, and does not have a stop codon in the same reading frame as the start codon.

[8] A method for producing protein in a prokaryotic cell expression system, comprising:

expressing a protein encoded by the cyclic RNA using the cyclic RNA described in [7] above as template.

Effects of the Invention

According to the cyclic RNA of the present invention and protein production method of the present invention that uses that cyclic RNA as template, long-chain protein having a target repetitive sequence can be synthesized efficiently. In particular, the realization of rotary protein translation that uses cyclic RNA as template even in human cells was made possible for the first time by the present invention.

BEST MODE FOR CARRYING OUT THE INVENTION

Figure 1:
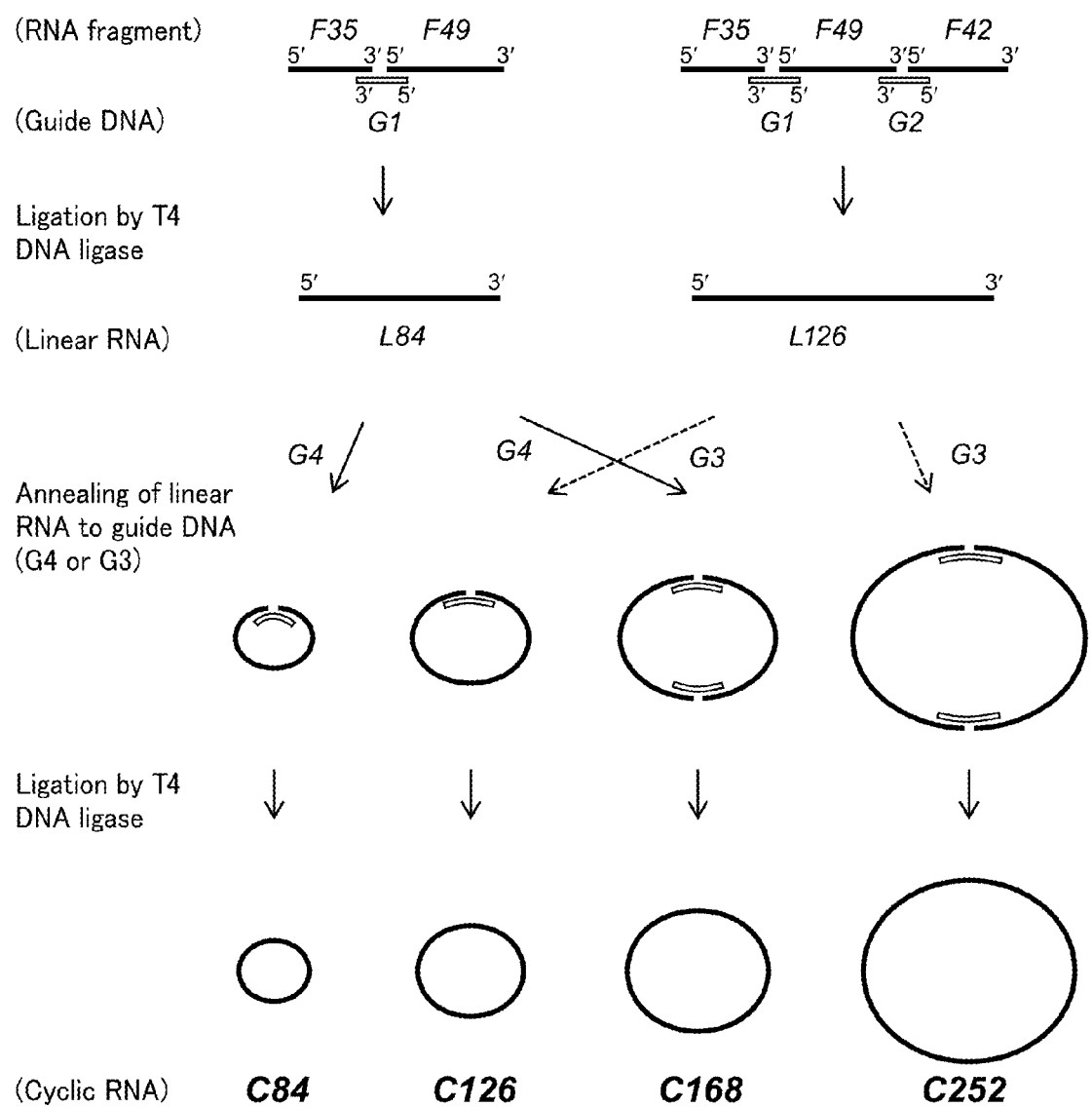
FIG. 1 is a drawing schematically showing the synthesis scheme of cyclic RNA synthesized in Example 1.

[Cyclic RNA for Eukaryotic Cell Translation System]

Among the cyclic RNA of the present invention, the cyclic RNA that serves as the template of rotary protein translation in a eukaryotic cell translation system (to also be referred to as "cyclic RNA for eukaryotic cells of the present invention") is characterized in that it encodes a protein, has a full-length number of bases of equal to or greater than 102 and is a multiple of 3, has at least one start codon, does not have a stop codon in the same reading frame as the start codon, and does not contain an IRES. An IRES refers to a ribosome binding site capable of functioning in place of a cap structure. The findings that rotary protein translation is possible in an animal cell translation system in the case of using cyclic RNA not having an IRES as template, and that rotary protein translation occurs in animal cells and not in a cell-free system, were first demonstrated by the inventors of the present invention.

In the case of cyclic RNA requiring an IRES, although the required ring size ends up becoming large at 256 bases (full length of the IRES), if the size of the cyclic RNA becomes excessively large, it becomes susceptible to the effects of decomposition and the like, thereby resulting in the risk of a decrease in stability of the cyclic RNA. Moreover, as a result of the IRES also being translated, protein repeats end up being synthesized that contain a large number of domains other than the target protein.

In contrast, the cyclic RNA for eukaryotic cells of the present invention does not require a ribosome binding site such as an IRES that is capable of functioning in place of a cap structure, thereby making it possible to minimize those sequences other than the domain encoded by the synthesized target protein. Consequently, in the case of using the cyclic RNA for eukaryotic cells of the present invention as template, the number of domains other than that of the target protein among the translated proteins can be reduced. For example, even in the case of cyclic RNA having only a linker consisting of 1 to 10 bases for linking the terminals of domains encoding a target protein into the shape of a ring, or cyclic RNA composed only of an ORF of a target protein to be synthesized, that cyclic RNA is able to function as template of rotary protein translation provided the full-length number of bases is equal to or greater than 102 and is a multiple of 3 and it has at least one start codon.

The full-length number of bases of the cyclic RNA for eukaryotic cells of the present invention is equal to or greater than 102 and is a multiple of 3. There is no shifting of the reading frame during translation since the full-length number of bases is a multiple of 3. In addition, although there are cases in which the cyclic RNA does not function as a template of a translation reaction in the case the full length of the cyclic RNA is excessively short, in the present invention, since the full-length number of bases is equal to or greater than 102, the cyclic RNA is able to function as a template of rotary protein translation. Although there are no particular limitations on the upper limit of the full-length number of bases of the cyclic RNA for eukaryotic cells of the present invention provided it is a length that enables the cyclic RNA to function as a template of rotary protein translation, in order to further increase translation efficiency, it is preferably 561 or less, more preferably 501 or less, even more preferably 450 or less, and still more preferably 402 or less.

The cyclic RNA for eukaryotic cells of the present invention has at least one start codon (such as AUG) for expressing a target protein. Although the cyclic RNA for eukaryotic cells of the present invention preferably only has one start codon from the viewpoint of homogeneity of the synthesized protein repeats, it may also have two or more start codons of the same reading frame. This is because, in the case of the same reading frame, although the protein repeat synthesized from each start codon has a different N-terminal portion, the same protein is repeatedly synthesized. On the other hand, in the case of the presence of an AUG of a reading frame that differs from that of the start codon for expressing a target protein, since protein repeats other than the target protein also end up being translated, the codon is preferably modified in this case so that an AUG of a different reading frame is not present.

The cyclic RNA for eukaryotic cells of the present invention does not have a stop codon in the same reading frame as the start codon for expressing a target protein. Consequently, a theoretically infinite number of protein repeats can be synthesized. Furthermore, the cyclic RNA may have a stop codon of a different reading frame from that of the start codon for expressing a target protein.

In addition, the cyclic RNA preferably has a Kozak sequence upstream from the start codon for expressing a target protein in order to improve translation efficiency. The specific base sequence of the Kozak sequence can be suitably determined in consideration of such factors as the base sequence of the domain that encodes the protein to be expressed and the biological species of the eukaryotic cells of the translation system.

[Cyclic RNA for Prokaryotic Cell Translation System]

Among the cyclic RNA of the present invention, the cyclic RNA serving as template of rotary protein translation in a prokaryotic cell translation system (to also be referred to as "cyclic RNA for prokaryotic cells of the present invention") is characterized in that, it encodes a protein, has a full-length number of bases that is from 102 to 360 and is a multiple of 3, has a single ribosome binding site recognized by ribosomes derived from prokaryotic cells, has at least one start codon (such as AUG) within 1 to 20 bases downstream from the ribosome binding site, and does not have a stop codon in the same reading frame as the start codon. Translation efficiency can be remarkably enhanced in a prokaryotic cell translation system as a result of the full-length number of bases being from 102 to 360.

Although the reason for the enhancement of translation efficiency as a result of making the full-length number of bases to be within the aforementioned range is not clear, since the domain in which ribosomes bind to RNA consists of 30 to 40 bases, translation is presumed to occur in the cyclic RNA for prokaryotic cells of the present invention as a result of only one ribosome binding to a single cyclic RNA. As a result of protein synthesis by a single ribosome in which only one ribosome binds to a single cyclic RNA, steric inhibitory effects between ribosomes that occur in polyribosomes are presumed to be nullified, thereby resulting in increased translation efficiency.

Similar to the cyclic RNA for eukaryotic cells of the present invention, since the full-length number of bases of the cyclic RNA for prokaryotic cells of the present invention is a multiple of 3, there are no shifts in the reading frame during translation. In addition, since the cyclic RNA does not have a stop codon in the same reading frame as the start codon for expressing a target protein, a theoretically infinite number of protein repeats can be synthesized.

The cyclic RNA for prokaryotic cells of the present invention has at least one ribosome binding site. There are no particular limitations on the ribosome binding site provided it is a site that is recognized by ribosomes derived from prokaryotic cells where those ribosomes are bound, and an example thereof is an SD sequence. The specific base sequence of the SD sequence can be determined in consideration of such factors as the biological species of the prokaryotic cells of the translation system used.

The cyclic RNA for prokaryotic cells of the present invention has a start codon within 1 to 20 bases downstream from the aforementioned ribosome binding site. Although the start codon possessed by the cyclic RNA for prokaryotic cells of the present invention is preferably only present within 1 to 20 bases downstream from the aforementioned ribosome binding site from the viewpoint of homogeneity of the synthesized protein repeats, it may also be present at another site. Even in the case the start codon is present at another site, a target protein repeat can be predominantly synthesized since translation from the start codon located immediately after the ribosome binding site is carried out preferentially.

[Synthesis of Cyclic RNA]

There are no particular limitations on the method used to synthesize the cyclic RNA for eukaryotic cells of the present invention or the cyclic RNA for prokaryotic cells of the present invention (which may be collectively referred to as the "cyclic RNA of the present invention"). For example, cyclic RNA can be synthesized by synthesizing single-stranded RNA by a known chemical synthesis reaction followed by ligating the single-stranded RNA with a ligase. Cyclic RNA can also be synthesized by synthesizing a plurality of single-stranded RNA followed by ligating each of these single-stranded RNA in a suitable order. When carrying out the ligase reaction, similar to the method used to synthesize cyclic RNA described in Non-Patent Document 2, the ligase reaction can be carried out efficiently by using a DNA probe that hybridizes with both ends of two single-stranded RNA to be ligated. In addition, cyclic RNA may also be prepared by using a splicing reaction similar to the method for synthesizing cyclic RNA described in Non-Patent Document 1.

In addition, cyclic RNA can also be synthesized with a transcription reaction using a polymerase. First, single-stranded RNA is synthesized by carrying out a transcription reaction with polymerase in a cell-free system using double-stranded DNA, which has a base sequence complementary to the target cyclic RNA to be synthesized downstream from a promoter sequence, as template. The target cyclic RNA can be synthesized by ligating the 5'-terminal and the 3'-terminal of the synthesized linear single-stranded RNA.

[Protein Synthesis]

A protein repeat having a protein encoded by the cyclic RNA for eukaryotic cells of the present invention as a repetitive sequence structure is translated and synthesized by introducing the cyclic RNA into eukaryotic cells or by adding to a cell-free expression system derived from eukaryotic cells.

Similarly, a protein repeat having a protein encoded by the cyclic RNA for prokaryotic cells of the present invention as a repetitive sequence structure is translated and synthesized by introducing the cyclic RNA into prokaryotic cells or by adding to a cell-free expression system derived from prokaryotic cells. In rotary protein translation using the cyclic RNA of the present invention as template, protein synthesis theoretically proceeds indefinitely once a ribosome binds to the cyclic RNA and initiates protein synthesis. In other words, the rate-limiting step of the start of translation is only at the time of the initial ribosomal binding, thereby resulting in the advantage of all subsequent protein synthesis being carried out efficiently.

There are no particular limitations on the method used to introduce the cyclic RNA of the present invention into eukaryotic cells or prokaryotic cells, and can be suitably selected in consideration of cell species from among known methods such as the calcium phosphate method, DEAF dextran method, lipofectin method or electroporation. Although there are no particular limitations on the cells introduced with the cyclic RNA for prokaryotic cells of the present invention provided they are prokaryotic cells, Escherichia coli cells are preferable since they are commonly used in expression of recombinant proteins and the like. In addition, there are no particular limitations on the cells introduced with cyclic RNA for eukaryotic cells of the present invention provided they are eukaryotic cells, and may be fungal cells such as yeast or mold, plant cells, insect cells or animal cells such as mammalian cells. For example, in the case of synthesizing a protein repeat to serve as a material of a pharmaceutical and the like to be applied to humans, human-derived cultured cells are used preferably.

The cell-free system to which the cyclic RNA of the present invention is added is an extracellular translation system that contains all components required for translation, such as ribosomes, tRNA and the like. More specifically, an extract of eukaryotic cells or prokaryotic cells can be used as a cell-free system. Any conventionally known eukaryotic and prokaryotic cells can be used for the aforementioned eukaryotic cells and prokaryotic cells, specific examples of which include *Escherichia coli*, thermophilic bacteria, wheat germ, rabbit reticulocytes, mouse L cells, Erlich ascites tumor cells, HeLa cells, CHO cells and budding yeast, and cells derived from *Escherichia coli* (such as *E. coli* S30 cell extract) or cells derived from thermophilic bacteria (*Thermus thermophilus*) are preferable since they allow the obtaining of a large synthesized quantity.

The *E. coli* S30 cell extract can be prepared in accordance with a known method from *E. coli* strains A19 (rna, met), BL21, BL21 Star, BL21-CodonPlus and the like (see Pratt, J. M. et al., Transcription and Translation—A Practical Approach (1984), pp. 179-209, Henes, B. D. and Higgins, S. J. ed., IRL Press, Oxford). In addition, commercial products available from Promega Corp. or Novagen Inc. may also be used. In addition, batch methods, flow methods and any other conventionally known technologies (see, for example, Spirin, A. et al., Methods in Enzymol., 217, 123-142, 1993) can also be applied.

Long-chain protein repeats can be synthesized easily by using the cyclic RNA of the present invention. Consequently, proteins such as silk or collagen having a repeat structure can be synthesized more easily as a result of the cyclic RNA of the present invention having a domain that encodes the repeat structure portion. In addition, in the case of cyclic RNA having a domain encoding a histidine tag or FLAG tag and the like in addition to a domain encoding a target protein, a protein repeat can be synthesized that has the tag peptide within the repetitive sequence structure. In this case, the synthesized protein repeat can be easily purified by using the tag peptide.

In the case the cyclic RNA of the present invention has a domain that encodes a target protein and a domain that encodes a peptide that is recognized and cleaved by a protease, a large number of molecules of the target protein can be obtained from a single molecule of a protein repeat by treating the protein repeat synthesized by using the cyclic RNA as template with protease. In addition, in the case of synthesizing a peptide having a comparatively low molecular weight, cyclic RNA may be used as template that ligates a plurality of domains encoding the peptide. Peptides can be synthesized in large volume by using cyclic RNA, in which is arranged a plurality of domains that encode peptide and a domain that encodes a peptide to be recognized and cleaved by a protease between those domains, as template.

Use of the cyclic RNA of the present invention can be applied to the preparation of medical materials and other functional materials. For example, since a physiologically active peptide can be made to be produced in cells by introducing the cyclic RNA of the present invention into those cells, the cyclic RNA of the present invention can be used as a novel pharmaceutical. In addition, it can also be used in principle as a signal amplification mechanism by forming protein repeats.

EXAMPLES

The following provides a detailed explanation of the present invention based on examples and comparative examples. However, the present invention is not limited by the following descriptions.

Example 1

Cyclic RNA for prokaryotic cells was synthesized having a domain encoding one or a plurality of FLAG peptides, and protein was synthesized in a cell-free system using these cyclic RNA as templates.

<Synthesis of Cyclic RNA>

(1) Preparation of Oligonucleotides

More specifically, four types of cyclic RNA or linear RNA fragments in the form of RNA oligonucleotides (F35, F49, F42 and F42') and five types of DNA oligonucleotides used as templates for a ligation reaction using the enzyme T4 DNA ligase (G1, G2, G3, G3' and G4') were respectively chemically synthesized. Furthermore, F42' has a base length of 48 and was obtained by adding UAAUAA to the 3'-terminal of F42. The sequence of each oligonucleotide is shown in Table 1 and SEQ ID NO: 1 to 9 of the sequence listings. In Table 1, the enclosed portion represents the ribosome binding sequence, bases indicated in bold letters (AUG) represent the start codon, underlined locations represent FLAG-encoding sequences, and the double underlined portion represents a stop codon. "p" indicates that the 5'-terminal is phosphorylated.

TABLE 1

| | Sequence | |
|---|---|---|
| F35 | 5' p-r(AUUAUU<u>AAGGAG</u>AUAUAUCCG AUG AUUAUUGA-CUA) 3' | SEQ ID NO: 001 |
| F49 | 5' p-r(CAAGGACGACGAUGACAAAAUUAUUGACUACAAG-GACGACGAUGACAAA) 3' | SEQ ID NO: 002 |
| F42 | 5' p-r(CUGCUGAUUAUUGACUACAAGGACGACGAUGACA-AAAUUAUU) 3' | SEQ ID NO: 003 |
| F42' | 5' p-r(CUGCUGAUUAUUGACUACAAGGACGACGAUGACA-AAAUUAUUUAAUAA) 3' | SEQ ID NO: 004 |
| G1 | 5' d(TCGTCCTTGTAGTCAATAAT) 3' | SEQ ID NO: 005 |
| G2 | 5' d(AATCAGCAGTTTGTCATC) 3' | SEQ ID NO: 006 |
| G3 | 5' d(CTCCTTAATAATAATAATTTTGTC) 3' | SEQ ID NO: 007 |
| G3' | 5' d(CTCCTTAATAATTTATTAAATAAT) 3' | SEQ ID NO: 008 |
| G4 | 5' d(CCTTAATAATTTTGTCATCG) 3' | SEQ ID NO: 009 |

All nine types of oligonucleotides were each synthesized with the H-8-SE DNA Synthesizer (GeneWorld Co., Ltd.) using β-cyanoethyl phosphoramidite reagent (Glen Research Corp.). A 2'-O-TOM protected form was used for the RNA amidite reagent. At that time, the 5'-terminals of all of the RNA oligonucleotides (F35, F49, F42 and F42') were monophosphorylated using a chemical phosphorylation reagent (Glen Research Corp.). All of the synthesized RNA were de-protected in accordance with established methods and purified by denaturing polyacrylamide gel electrophoresis (PAGE). On the other hand, the DNA oligonucleotides (G1, G2, G3, G3' and G4) were de-protected in accordance with established methods following synthesis and purified with the Micropure® II Cartridge (Biosearch Technologies Inc.) filter cartridge.

(2) Synthesis Scheme

Cyclic RNA consisting of 84 bases having a domain that encodes two molecules of FLAG peptide (C84) and cyclic RNA consisting of 168 bases having a domain that encodes four molecules of FLAG peptide (C168) were synthesized by ligating F35 and F49 using G1 and G4 as templates. Cyclic RNA consisting of 126 bases having a domain that encodes three molecules of FLAG peptide (C126) and cyclic RNA consisting of 252 bases having a domain that encodes six molecules of FLAG peptide (C252) were synthesized by ligating F35, F49 and F42 using G1, G2 and G3 as templates. Each synthesis scheme is schematically shown in FIG. 1.

In addition, linear RNA consisting of 126 bases having a domain that encodes three molecules of FLAG peptide (L126) was synthesized by ligating F35, F49 and F42 using G1 and G2 as templates. Linear RNA consisting of 132 bases having a domain that encodes three molecules of FLAG peptide and a stop codon (L126+stop) was synthesized by ligating F35, F49 and F42' using G1 and G2 as templates, and cyclic RNA consisting of 132 bases having a domain that encodes three molecules of FLAG peptide and a stop codon (C126+stop) was synthesized by ligating F35, F49 and F42' using G1, G2 and G3' as templates.

The sequences of C84, C125, C168, C252 and C126+stop are shown in Table 2 and SEQ ID NO: 10 to 14 of the sequence listings. In Table 2, the enclosed portions represent ribosome binding sequences, bases indicated in bold letters (AUG) represent a start codon, underlined locations represent FLAG-encoding sequences, and the double underlined portion represents a stop codon. In addition, each of these cyclic RNA form a cyclic structure ligated at both ends of the 5'-terminal and 3'-terminal. Furthermore, although L126 and L126+stop have the same base sequences as C126 and C126+stop, respectively, they are linear RNA that do not have a cyclic structure.

TABLE 2

| | Sequence | |
|---|---|---|
| C84 | (5')-r(AUUAUU<u>AAGGAG</u>AUAUAUCCG AUG AUUAUUGACU-ACAAGGACGACGAUGACAAAAUUAUUGACUACAAGGACGACGA-UGACAAA-(3') | SEQ ID NO: 010 |
| C126 | (5')-r(AUUAUU<u>AAGGAG</u>AUAUAUCCG AUG AUUAUUGACU-ACAAGGACGACGAUGACAAAAUUAUUGACUACAAGGACGACGA-UGACAAACUGCUGAUUAUUGACUACAAGGACGACGAUGACAAA-AUUAUU-(3') | SEQ ID NO: 011 |
| C126+stop | (5')-r(AUUAUU<u>AAGGAG</u>AUAUAUCCG AUG AUUAUUGACU-ACAAGGACGACGAUGACAAAAUUAUUGACUACAAGGACGACGA-UGACAAACUGCUGAUUAUUGACUACAAGGACGACGAUGACAAA-AUUAUUUAAUAA)-(3') | SEQ ID NO: 012 |
| C168 | (5')-r(AUUAUU<u>AAGGAG</u>AUAUAUCCG AUG AUUAUUGACU-ACAAGGACGACGAUGACAAAAUUAUUGACUACAAGGACGACGA-UGACAAAAUUAUU<u>AAGGAG</u>AUAUAUCCG AUG AUUAUUGACU-ACAAGGACGACGAUGACAAAAUUAUUGACUACAAGGACGACGA-UGACAAA)-(3') | SEQ ID NO: 013 |

TABLE 2-continued

| | Sequence | |
|---|---|---|
| C252 | (5')-r(AUUAUU|AAGGAG|AUAUAUCCG AUG AUUAUUGAC-<br>UACAAGGACGACGAUGACAAAAUUAUUGACUACAAGGACGACG-<br>AUGACAAACUGCUGAUUAUUGACUACAAGGACGACGAUGACAA-<br>AAUUAUUAUUAUU|AAGGAG|AUAUAUCCG AUG AUUAUUGACU-<br>ACAAGGACGACGAUGACAAAAUUAUUGACUACAAGGACGACGA-<br>UGACAAACUGCUGAUUAUUGACUACAAGGACGACGAUGACAAA-<br>AUUAUU)-(3') | SEQ ID NO: 014 |

(3) Synthesis of L126

L126 was synthesized by ligating F35, F39 and F42 using G1 and G2 as templates. The ligase reaction was carried out in a reaction liquid (reaction liquid volume: 1.7 mL) containing 5 µM F35, 5 µM F49, 15 µM F42, 10 µM G1, 20 µM G2, 35 units/µL of T4 DNA ligase (Takara Bio Inc.), 66 mM Tris-HCl (pH 7.6), 6.6 mM MgCl₂ 10 mM DTT, 0.1 mM ATP and 10% (w/v) PEG6000.

Figure 2:
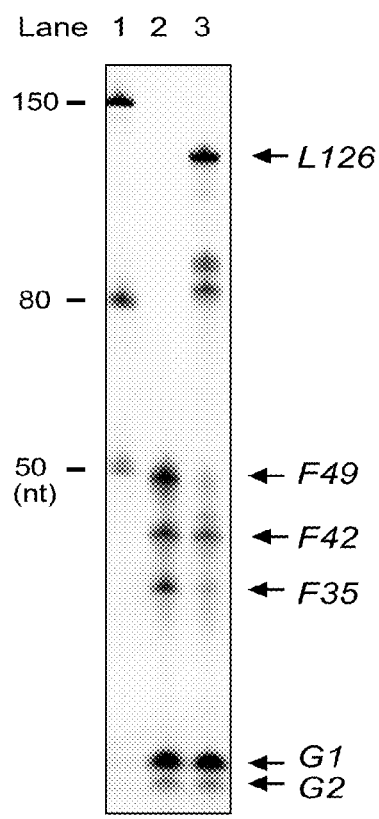
FIG. 2 is an image of stained nucleic acids obtained as a result of denaturing PAGE following a ligase reaction for synthesizing L126 in Example 1.

More specifically, after heating the reaction liquid to which all components had been added except for the PEG6000 and T4 DNA ligase for 3 minutes at 90° C., the reaction liquid was allowed to slowly cool to room temperature. Subsequently, the PEG6000 and T4 DNA ligase were added to the reaction liquid followed by incubating for about 5 hours at 37° C. After extracting and removing the PEG6000 by adding an equal volume of chloroform to the reaction liquid, 3 M aqueous sodium acetate solution (pH 5.2) and isopropyl alcohol were added followed by cooling to precipitate and recover RNA. After analyzing a portion of the recovered RNA by denaturing PAGE (8% polyacrylamide, 7.5 M urea, 25% formamide, 1×TBE) and visualizing by staining the gel with SYBR® Green II (Takara Bio Inc.) stain to confirm progression of the ligase reaction, the ligation product (L126) was isolated from the remaining RNA using the same denaturing PAGE. After visualizing the band containing the target product by UV shadowing, cutting out the band and finely crushing, the RNA was extracted twice with 1 mL of eluate (10 mM EDTA (pH 8.0)). The resulting extract was concentrated with a centrifugal evaporator and further concentrated using the Microcon® YM-3 (Millipore Corp.) centrifugal filter. RNA was desalted and recovered from the aforementioned extract following concentration by alcohol precipitation. The resulting RNA (L126) was dissolved in ultrapure water and suitably diluted followed by measurement of the UV absorption spectrum and calculation of yield (recovered amount: 2.17 nmol, yield: 26%). FIG. 2 shows a stained image obtained as a result of staining nucleic acids present in denaturing PAGE gel with SYBR® Green II (Takara Bio Inc.) strain. An ssRNA marker was applied to Lane 1, the reaction liquid prior to the enzyme reaction was applied to Lane 2, and the reaction liquid following the enzyme reaction was applied to Lane 3. As shown in FIG. 2, L126 composed of F35, F49 and F42 was synthesized following the enzyme reaction.

(4) Synthesis of C126

C126 was synthesized by making L126 cyclical by a ligase reaction. The ligase reaction was carried out in a reaction liquid (reaction liquid volume: 2 mL) containing 1 µM L126, 1 µM G3, 17.5 units/µL of T4 DNA ligase (Takara Bio Inc.), 6 mM Tris-HCl (pH 7.6), 6.6 mMMgCl₂, 10 mMDTT, 0.1 mM ATP and 10% (w/v) PEG6000.

Figure 3:
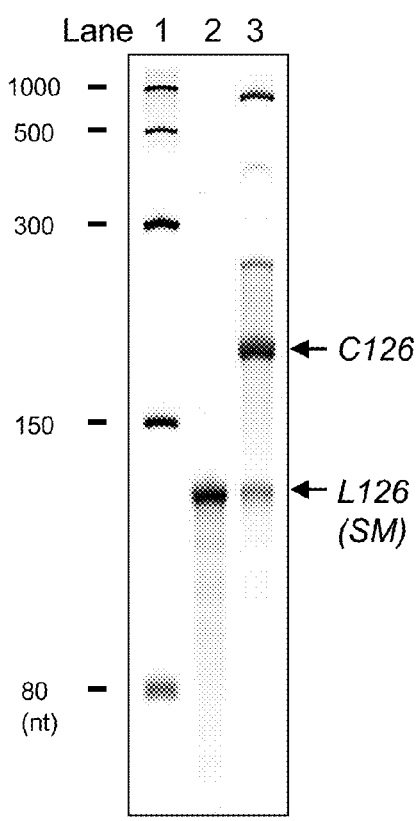
FIG. 3 is a stained image of nucleic acid staining following electrophoresis of reaction products following a ligase reaction for synthesizing C126 in Example 1.

More specifically, after heating the reaction liquid to which all components had been added except for the PEG6000 and T4 DNA ligase for 3 minutes at 90° C., the reaction liquid was allowed to slowly cool to room temperature. Subsequently, the PEG6000 and T4 DNA ligase were added to the reaction liquid followed by incubating for about 7 hours at 37° C. After extracting and removing the PEG6000 by adding an equal volume of chloroform to the reaction liquid, 3 M aqueous sodium acetate solution (pH 5.2) and isopropyl alcohol were added followed by cooling to precipitate and recover RNA. After analyzing a portion of the recovered RNA by denaturing PAGE (6% polyacrylamide, 7.5 M urea, 25% formamide, 1×TBE) and visualizing by staining the gel with SYBR® Green II (Takara Bio Inc.) stain to confirm progression of the ligase reaction, the ligation product (C126) was isolated from the remaining RNA using the same denaturing PAGE. After visualizing the band containing the target product by UV shadowing, cutting out the band and finely crushing, the RNA was extracted twice with 0.5 mL of eluate (10 mM EDTA (pH 8.0)). The resulting extract was concentrated with a centrifugal evaporator and further concentrated using the Microcon® YM-3 (Millipore Corp.) centrifugal filter. RNA was desalted and recovered from the aforementioned extract following concentration by alcohol precipitation. The resulting RNA (C126) was dissolved in ultrapure water and suitably diluted followed by measurement of the UV absorption spectrum and calculation of yield (recovered amount: 0.40 nmol, yield: 20%). FIG. 3 shows a stained image obtained as a result of staining the denaturing PAGE gel with SYBR® Green II (Takara Bio Inc.) stain. An ssRNA marker was applied to Lane 1, the reaction liquid prior to the enzyme reaction was applied to Lane 2, and the reaction liquid following the enzyme reaction was applied to Lane 3. As shown in FIG. 3, C126 was synthesized from L126 following the enzyme reaction.

(5) Synthesis of L126+Stop and C126+Stop

L126+stop and C126+stop were synthesized in the same manner as in the aforementioned sections (2) and (3) with the exception of using F42' instead of F42 and G3' instead of G3, respectively.

(6) Synthesis of C84, C168 and C252

C84, C168 and C252 were synthesized in the same manner as the synthesis of L126 described in the aforementioned section (3) and the synthesis of C126 described in the aforementioned section (4) with the exception of suitably using each of the fragments shown in FIG. 1 and described in the aforementioned section (2).

Figure 4:
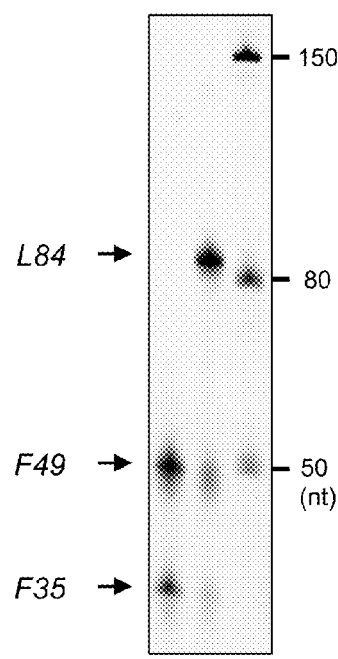
FIG. 4 is a stained image of nucleic acid staining following electrophoresis of reaction products of a ligase reaction for synthesizing L84 in Example 1.

FIG. 4 shows a stained image obtained as a result of analyzing the reaction product of the ligase reaction for synthesizing L84 (linear RNA consisting of 84 bases having a domain that encodes two molecules of FLAG peptide) by 8% denaturing PAGE. The reaction liquid prior to the enzyme reaction was applied to Lane 1, the reaction liquid following the enzyme reaction was applied to Lane 2, and an ssRNA marker was applied to Lane M. As shown in FIG. 4, L84 was synthesized from F35 and F49 following the enzyme reaction.

Figure 5:
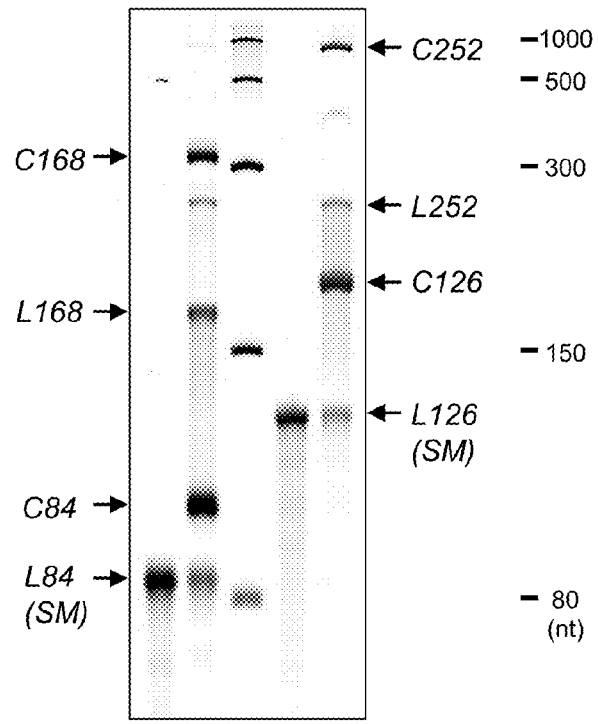
FIG. 5 is a stained image of nucleic acid staining following electrophoresis of reaction products of ligase reactions for synthesizing C84, C168, C126 and C252 in Example 1.

FIG. 5 shows a stained image obtained as a result of analyzing the reaction product of the cyclic RNA synthesis reaction by 8% denaturing PAGE. The reaction liquid prior to the ligase reaction using L84 as template was applied to Lane 1, the reaction liquid following the ligase reaction using L84 as template was applied to Lane 2, the reaction liquid prior to the ligase reaction using L126 as template was applied to Lane 3, and the reaction liquid following the ligase reaction using L126 as template was applied to Lane 4. As shown in FIG. 5, C84 and C168 were synthesized from L84, and C126 and C252 were synthesized from L126.

<Protein Synthesis Using Cyclic RNA as Template>

Figure 6:
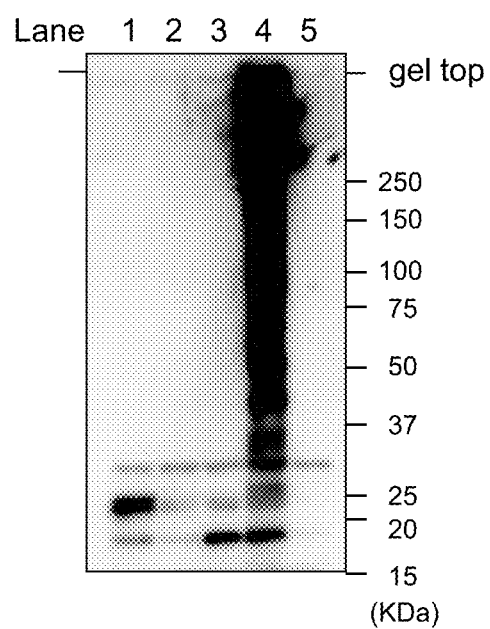
FIG. 6 is a stained image of protein bands containing FLAG obtained as a result of electrophoresis of reaction liquids of cell-free translation reactions using L126, L126+stop, C126 and C126+stop as templates in Example 1.

(7) Cell-Free Translation Reactions Using L126, L126+ Stop, C126 and C126+Stop as Templates L126, L126+stop, C126 and C126+stop were added to cell-free translation liquid (PURExpress® in vitro protein synthesis kit, New England Biolabs Inc.) to a concentration of 1 μM followed by incubating for 3 hours at 37° C. An RNA-free reaction liquid was incubated in the same manner as a control. A 1 μL aliquot was sampled from the reaction liquid and mixed with 5 μL of 2× sample buffer (0.125 M Tris-HCl (pH 8.0), 2% SDS, 30% glycerol, 0.02% bromophenol blue, 5% 2-mercaptoethanol) and 4 μL of purified water. After heating for 5 minutes at 95° C., the reaction liquid was electrophoresed using 10% to 20% gradient polyacrylamide gel (Atto Corp.) (phoresis buffer: 25 mM Tris-HCl, 0.1% SDS, 192 mM glycine). After transferring the protein that developed in the gel onto a PVDF membrane (Millipore Corp.), the protein was reacted with mouse-produced anti-FLAG antibody and anti-mouse IgG antibody-peroxidase (HRP) complex (both available from Sigma-Aldrich Corp.) and bands specific to FLAG sequence were visualized (Light-Capture, Atto Corp.) using HRP substrate (SuperSignal® chemiluminescent substrate for detection by Western blot analysis, West Femto Maximum Sensitivity Substrate, Thermo Inc.). FIG. 6 shows the results of visualizing proteins containing FLAG. Reaction liquid containing L126 was applied to Lane 1, reaction liquid containing L126+stop was applied to Lane 2, reaction liquid containing C126+stop was applied to Lane 3, reaction liquid containing C126 was applied to Lane 4, and RNA-free reaction liquid was applied to Lane 5. As shown in FIG. 6, a large amount of protein having a much longer chain length than the proteins of 15 kDa to 20 kDA synthesized in the reaction liquids containing C126+stop and L126 was expressed in the reaction liquid containing C126. In particular, protein of 250 kDa or more was expressed, and protein repeats were suggested to be synthesized in the case of C126 as a result of the translation reaction proceeding continuously due to ribosomes rotating 10 times or more.

(8) Cell-Free Translation Reactions Using C84, C126, C168 and C252 as Templates

Figure 7:
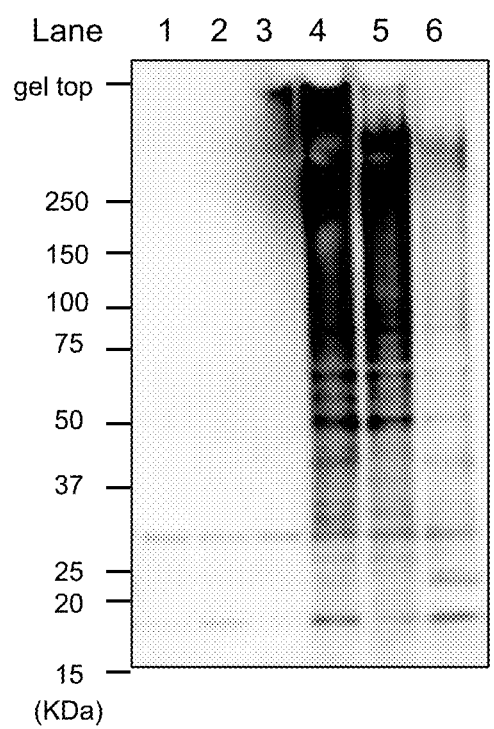
FIG. 7 is a stained image of protein bands containing FLAG obtained as a result of electrophoresis of reaction liquids of cell-free translation reactions using C84, C126, C168 and C252 as templates in Example 1.

Cell-free translation reactions were carried out in the same manner as the aforementioned section (7) with the exception of using C84, C126, C168 and C252 as templates, followed by electrophoresing the reaction liquids using 10% to 20% gradient polyacrylamide gel, transferring the protein that developed in the gel to a PVDF membrane, and visualizing those bands specific to the FLAG sequence. FIG. 7 shows the results of visualizing protein bands containing FLAG. RNA-free reaction liquid was applied to Lanes 1 and 3, reaction liquid containing C84 was applied to Lane 2, reaction liquid containing C126 was applied to Lane 4, reaction liquid containing C168 was applied to Lane 5, and reaction liquid containing C252 was applied to Lane 6. As shown in FIG. 7, in the case of using C84 as template, the reaction product of a continuous translation reaction in the form of a long-chain peptide was not formed. On the other hand, in the case of using C126, C168 and C252 as templates, the reaction product of a continuous translation reaction in the form of a long-chain peptide (protein repeat) was observed to have been formed. In the case of using C126 and C168 as templates in particular, translation efficiency was higher and a larger number of protein repeats were synthesized in comparison with the case of using C252 as template.

Example 2

Cyclic RNA for eukaryotic cells was synthesized having a domain that encodes a plurality of FLAG peptides, and protein was synthesized in a cell-free system derived from rabbits using these cyclic RNA as templates.

<Synthesis of Cyclic RNA>

Cyclic RNA for eukaryotic cells was synthesized by a transcription reaction using polymerase. First, DNA oligonucleotides were synthesized using a DNA synthesizer (Fragments 1 to 3 in Table 3, and the sequences thereof are shown in SEQ ID NO: 15 to 17), and after ligating with T4 DNA ligase, double-stranded DNA oligonucleotides having 155, 284, 290 and 413 base pairs (template DNA) were synthesized by annealing or PCR (Tables 4 and 5). Next, in vitro transcription was carried out with RNA polymerase using the double-stranded DNA oligonucleotides as templates to synthesize linear single-stranded RNA composed of 129, 258, 264 and 387 bases (Tables 6 and 7), followed by ligating the 5'-terminal and 3'-terminal using T4 RNA ligase to synthesize cyclic RNA. The following provides a description of the details thereof.

(1) Preparation of Oligonucleotides

The sequences of each of the types of oligonucleotides used as templates of the polymerase reaction are shown in Table 3. In Table 3, "p" indicates that the 5'-terminal is phosphorylated.

In Table 3, DNA oligonucleotides were synthesized with the H-8-SE DNA Synthesizer (GeneWorld Co., Ltd.) using β-cyanoethyl phosphoramidite reagent (Glen Research Corp.). The 5'-terminal of Fragment 1 and Fragment 2 was monophosphorylated using a chemical phosphorylation reagent (Glen Research Corp.). Each of the oligonucleotides was de-protected in accordance with established methods and purified with the Micropure® II Cartridge (Biosearch Technologies Inc.) filter cartridge. Fragment 1, Fragment 2, Fragment 3 and Fragment 1 DNA sense were further purified by denaturing PAGE.

TABLE 3

| | Sequence | |
|---|---|---|
| Fragment 1 | 5'_p-d(ACT TTA TCG TCG TCT TTA TAG TCA ATT ATC TTG TCG TCG TCG TGC TTG TAG TCG ATG ATC TTG TCG TGG TCG TCC TTG TAG TCG ATG ATC TTG TCG TCG TCG TCC TTC TAG TCC ATG GTG GCT CCC TAT AGT GAG TCG TAT TAG GAT CCG CG)3' | SEQ ID NO: 015 |

TABLE 3-continued

| | Sequence | |
|---|---|---|
| Fragment 2 | 5'p-d(ATC TGG TTG AAT TTA TCG TCG TGG TCT TTG TAG TCT ATA ATC TTG TCG TCG TCG TCC TTG TAG TCG ATG ATC TTG TCG TCG TCG TCC TTG ATAG TCG TG ATC TTG TCG TCG TCG TCT TTA TAG TCC AGT)3' | SEQ ID NO: 016 |
| Fragment 3 | 5' d(CCT CTA GAG GGT TTA TCG TCG TCG TCC TTG TAA TCT ATT ATC TTG TCG TCG TCG TCC TTG TAG TCG ATG ATC TTG TCG TCG TCG TCC TTG TAG TCG ATG ATC TTG TCG TCG TCG TCC TTA TAA TCG GAT)3' | SEQ ID NO: 017 |
| Adaptor 1(for 4x FLAG RNA) | 5' d(GGT GGC TCC CAC TTT ATC GT)3' | SEQ ID NO: 018 |
| Adaptor 2(for 8x FLAG RNA) | 5' d(GGT GGC TCC CAT CTG GTT GA)3' | SEQ ID NO: 019 |
| Adaptor 3(for 12x FLAG RNA) | 5' d(GGT GGC TCC CCC TCT AGA GG)3' | SEQ ID NO: 020 |
| Foward primer 1 | 5' d(CGC GGA TCC TAA TAC GAC TCA CTA TAG GGA GCC ACC ATG G)3' | SEQ ID NO: 021 |
| Adaptor oligo 1 | 5' d(ACG ATA AAG TAC TGG ACT AT)3' | SEQ ID NO: 022 |
| Adaptor oligo 2 | 5' d(TCA ACC AGA TAT CCG ATT AT)3' | SEQ ID NO: 023 |
| Reverse primer 1 | 5' d(CCT CTA GAG GGT TTA)3' | SEQ ID NO: 024 |
| Reverse primer 2 | 5' d(ATC TGG TTG AAT TTA)3' | SEQ ID NO: 025 |
| Fragment 1 DNA sense | 5' d(CGC GGA TCC TAA TAC GAC TCA CTA TAG GGA GCC ACC ATG GAC TAC AAG GAC GAC CAC GAG AAG ATC ATC GAC TAC AAG GAC GAC GAC GAC AAG ATC ATC GAC TAC AAG GAC GAC GAC GAC AAG ATA ATT GAC TAT AAA GAC GAC GAC GAT AAA GT)3' | SEQ ID NO: 026 |
| Reverse primer 3 | 5' d(TTC TGG TTG AAT TTA TC)3' | SEQ ID NO: 027 |
| Reverse primer 4 | 5' d(TTT CAG TTG AAT TTA TC)3' | SEQ ID NO: 028 |
| Adaptor 4 (for 8x FLAG(2) RNA) | 5' d(GGT GGC TCC CTT CTG GTT GA)3' | SEQ ID NO: 029 |
| Adaptor 4 (for 8x FLAG(stop) RNA) | 5' d(GGT GGC TCC CTT TCA GTT GA)3' | SEQ ID NO: 030 |
| Reverse primer 5 | 5' d(TCT TCC TTT CCG TTG AAT TTA TC)3' | SEQ ID NO: 031 |
| Reverse primer 6 | 5' d(TCT TAC TAT CAG TTG AAT TTA TC)3' | SEQ ID NO: 032 |
| Adaptor 6 (for 8x FLAG(3) circular RNA) | 5' d(GGT GGC TCC CTC TTA CTA TC)3' | SEQ ID NO: 033 |
| Adaptor 7 (for 8x FLAG(3 circular stop) RNA) | 5' d(GGT GGC TCC CTC TTA CTA TC)3' | SEQ ID NO: 034 |
| Foward primer 2 | 5' d(CGC GGA TCC TAA TAC GAC TC)3' | SEQ ID NO: 035 |

(2) Synthesis of Template DNA of In Vitro Transcription Reactions

Template DNA of in vitro transcription reactions described in Tables 4 and 5 was synthesized using the various types of oligonucleotides described in Table 3 and SEQ ID NO: 18 to 35 of the sequence listings. Underlined locations in Tables 4 and 5 indicate T7 promoter sequences.

TABLE 4

| | Base Length (b) | Sequence | |
|---|---|---|---|
| 4 x FLAG DNA | 155 | CGCGGATCC<u>TAATACGACTCACTATAGGG</u>AGCC ACCATGGACTACAAGGACCACGACGACAAGATC ATCGACTACAAGGACGACGACGACAAGATCATG ACTACAAGGACGACGACGACAAGATAATTGACT ATAAAGACGACGACGATAAAGT | SEQ ID NO: 036 |
| 8 x FLAG DNA | 284 | CGCGGATCC<u>TAATACGACTCACTATAGGG</u>AGCC ACCATGGACTACAAGGACGACGACGACAAGATC ATCGACTACAAGGAGGACGACGACAAGATCATC GACTACAAGGACGACGACGACAAGATAATTGAC TATAAAGA CGACGACGATAAGTACTGGACTAT AAAGACGACGACGACAAGATCATCGACTACAAG GACGACGACGACAAGATCATCGACTACAAGGAC GACGACGACAAGATTATAGACTACAAAGACGAC GACGATAAATTCAACCAGAT | SEQ ID NO: 037 |
| 12 x FLAG DNA | 413 | CGCGGATCC<u>TAATACGACTCACTATAGGG</u>AGCC AGCATGGACTACAAGGACGACGACGACAAGATC ATCGACTACAAGGACGACGACGACAAGATCATC GACTACAAGGACGACGACGACAAGATAATTGAC TATAAAGACGACGACGATAAAGTACTGGACTAT AAAGACGACGACGACAAGATCATCGACTACAAG GACGACGACGACAAGATCATCGACTACAAGGAC GACGACGACAAGATTATAGACTACAAAGACGAC GACGATAAATTCAACCAGATATCCGATTATAAG GACGACGACGACAAGATGATCGACTACAAGGAC GACGACGACAAGATCATCGACTACAAGGACGAC GACGACAAGATAATAGATTACAAGGACGACGAC GATAAACCCTCTAGAGG | SEQ ID NO: 038 |
| 8 x FLAG (2) DNA | 284 | CGCGGATCC<u>TAATACGACTCACTATAGGG</u>AGCC ACCATGGACTACAAGGACGACGACGACAAGATC ATCGACTACAAGGACGACGACGACAAGATCATC GACTACAAGGACGACGACGACAAGATAATTGAC TATAAAGACGACGACGATAAAGTACTGGACTAT AAAGACGACGACGACAAGATCATCGACTACAAG GACGACGACGACAAGATCATCGACTACAAGGAC GACGACGACAAGATTATAGACTACAAAGACGAC GACGATAAATTCAACCAGAA | SEQ ID NO: 039 |
| 8 x FLAG (stop) DNA | 284 | CGCGGATCC<u>TAATACGACTCACTATAGGG</u>AGCC ACCATGGACTACAAGGACGACGACGACAAGATC ATCGACTACAAGGACGACGACGACAAGATCATC GACTACAAGGACGACGACGACAAGATAATTGAC TATAAAGACGACGACGATAAAGTACTGGACTAT AAAGACGACGACGACAAGATCATCGACTAGAAG GACGACGACGACAAGATCATCGACTACAAGGAC GACGACGACAAGATTATAGACTACAAAGACGAC GACGATAAATTCAACTGAAA | SEQ ID NO: 040 |

TABLE 5

| | Base Length (b) | Sequence | |
|---|---|---|---|
| 8 x FLAG (3) DNA | 290 | CGCGGATCC<u>TAATACGACTCACTATAGGG</u>AGCCAC CATGGACTACAAGGACGACGACGACAACATCATCG ACTACAAGGACGACGACGACAAGATCATCGACTAC AAGGACGACGACGACAAGATAATTGACTATAAAGA CGACGACGATAAAGTACTGGACTATAAAGACGACG ACGACAAGATCATCGACTACAAGGACGACGACGAC AAGATCATCGACTACAAGGACGACGACGACAAGAT | SEQ ID NO: 041 |

TABLE 5-continued

| | Base Length (b) | Sequence | |
|---|---|---|---|
| | | TATAGACTACAAAGACGACGACGATAAATTCAACG GAAAGGAAGA | |
| 8 × FLAG (3 stop) DNA | 290 | CGCGGATCCT<u>AATACGACTCACTATAGGG</u>AGGCAC CATGGACTAC<u>AAGGACGACGACGACAAGATCATCG ACTACAAGGACCACCACGACAAGATCATCGACTAC AAGGACGACGACGACAAGATAA</u>TTGACTATAAGA CGACGACGATAAAGTACTGGACTATAAAGACGACG ACGACAAGATCATCGACTAC<u>AAGGACGACGACGAC AAGATCATCGACTACAAGGACGACGACGACAAGAT TATAGACTACAAAGACGACGACGATAAATTCAACT</u> <u>GATAGTAAGA</u> | SEQ ID NO: 042 |

4× FLAG DNA (SEQ ID NO: 36) was obtained by heating a reaction liquid containing mixed DNA consisting of 5.22 μm Fragment 1 (SEQ ID NO: 15) and Fragment 2 (SEQ ID NO: 16) (mixing molar ratio: 1:1), 40 mM Tris-HCl (pH 8.0), 8 mM MgCl$_2$ and 2 mM spermidine for 3 minutes at 90° C., followed by allowing to slowly cool to room temperature.

8× FLAG DNA (SEQ ID NO: 37) was obtained by ligating Fragment 1 (SEQ ID NO: 15) and Fragment 2 (SEQ ID NO: 16) using Adaptor 1 (SEQ ID NO: 18) as template and T4 DNA ligase, synthesizing an antisense strand by purifying the resulting ligation product by denaturing PAGE, synthesizing double-stranded DNA from the antisense strand and Forward Primer 1 (SEQ ID NO: 21) using PrimeSTAR® HS DNA Polymerase (Takara Bio Inc.), and purifying with the QIAquick® PCR Purification Kit (Qiagen Corp.).

12× FLAG DNA (SEQ ID NO: 38) was obtained by ligating Fragment 1 (SEQ ID NO: 15) Fragment 2 (SEQ ID NO:16) and Fragment 3 (SEQ ID NO: 17) using Adaptor 2 (SEQ ID NO: 19) and Adaptor 3 (SEQ ID NO: 20) as templates and T4 DNA ligase, synthesizing an antisense strand by purifying the resulting ligation product by denaturing PAGE, synthesizing double-stranded DNA from the antisense strand and Forward Primer 1 (SEQ ID NO: 21) using PrimeSTAR® HS DNA Polymerase (Takara Bio Inc.), and purifying with the QIAquick® PCR Purification Kit (Qiagen Corp.).

8× FLAG(2) DNA (SEQ ID NO: 39) and 8× FLAG(stop) DNA (SEQ ID NO: 40) were obtained by synthesizing double-stranded DNA by PCR using 12× FLAG DNA (SEQ ID NO: 38) as template and respectively using Forward Primer 1 (SEQ ID NO: 21) and Reverse Primer 3 (SEQ ID NO: 24) or Forward Primer 1 (SEQ ID NO: 21) and Reverse Primer 4 (SEQ ID NO: 28) as primers using PrimeSTAR® HS DNA Polymerase (Takara Bio Inc.), and purifying with the QIAquick® PCR Purification Kit (Qiagen Corp.).

8× FLAG(3) DNA (SEQ ID NO: 41) was obtained by synthesizing double-stranded DNA by PCR using 8× FLAG (2) DNA (SEQ ID NO: 39) as template and using Forward Primer 2 (SEQ ID NO: 35) and Reverse Primer 5 (SEQ ID NO: 31) as primers using PrimeSTAR® HS DNA Polymerase (Takara Bio Inc.), and purifying with the QIAquick® PCR Purification Kit (Qiagen Corp.).

8× FLAG(3 stop) DNA (SEQ ID NO: 42) was obtained by synthesizing double-stranded DNA by PCR using 8× FLAG (stop) DNA (SEQ ID NO: 40) as template and using Forward Primer 2 (SEQ ID NO: 35) and Reverse Primer 6 (SEQ ID NO: 32) as primers using PrimeSTAR® HS DNA Polymerase (Takara Bio Inc.), and purifying with the QIAquick® PCR Purification Kit (Qiagen Corp.).

(3) Synthesis of Linear Transcribed RNA by In Vitro Transcription Reaction

Linear transcribed RNA described in Tables 6 and 7 was synthesized using the template DNA described in Table 4. In Tables 6 and 7, the enclosed portions represent the Kozak sequences, bases indicated in bold letters (AUG) represent the start codon, underlined locations represent FLAG-encoding sequences, and the double underlined portions represent a stop codon (UGA, UAG, UAA).

TABLE 6

| | Base Length (b) | Sequence | |
|---|---|---|---|
| 4× FLAG RNA | 129 | GGGA|GCCACC| AUG <u>GACUACAAGGACGACGACGACAAG AUCAUCGACUACAAGGACGACGACGACAAGAUCAUCGAC UACAAGGACGACGACGACAAGAUAA</u>UUGACUAUAAAGAC GACGA CGAUAAAGU | SEQ ID NO: 043 |
| 8× FLAG RNA | 256 | GGGA|GCCACC| AUG <u>GACUACAAGGACGACGACGACAAG AUCAUCGACUACAAGGACGACGACGACAAGAUCAUCGAC UACAAGGACGACGACGACAAGAUAA</u>UUGACUAUAAAGAC GACGACGAUAAAGUACUGGACUAUAAAGACGACGACGAC AAGAUCAUCGACUACAACGACGACGACGACAAGAUCAUC GACUACAAGGACGACGACGACAAGAUUAUAGACUACAAA | SEQ ID NO: 044 |

TABLE 6-continued

| | Base Length (b) | Sequence | |
|---|---|---|---|
| 12× FLAG RNA | 387 | GGGA GCCACC AUG GACUACAAGGACGACGACGACAAG<br>AUCAUCGACUACAAGGACGACGACGACAAGAUCAUCGAC<br>UACAAGGACGACGACGACAAGAUAAUUGACUAUAAAGAC<br>GACGACGAUAAAGUACUGGACUAUAAAGACGACGACGA<br>AAGAUCAUCGACUACAAGGACGACGACGACAAGAUCAUC<br>GACUACAAGGACGAGGAGGACAAGAUUAUAGACUACAAA<br>GACGACGACGAUAAAUUCAACCAGAUAUCCGAUUAUAAG<br>GACGACGACGACAAGAUCAUCGACUACAAGGACGACGAC<br>GACAAGAUCAUCGACUACAAGGACGACGACGACAAGAUA<br>AUAGAUUACAAGGACGACGACGAUAAACCCUCUAGAGG | SEQ ID NO: 045 |
| 8× FLAG (2) RNA | 258 | GGGA GCCACC AUG GACUACAAGGACGACGACGACAA<br>GAUCAUCGACAUCAAGGACGACGACGACAAGAUCAUCGA<br>CUACAAGGACGACGACGACAAGAUAAUUGACUAUAAAGA<br>CGACGACGAUAAAGUACUGGACUAUAAAGACGACGACGA<br>CAAGAUCAUCGACUACAAGGACGACGACGACAAGAUCAU<br>CGACUACAAGGACGACGACGACAAGAUUAUAGACUACAA | SEQ ID NO: 046 |
| 8× FLAG (stop) RNA | 258 | GGGA GCCACC AUG GACUACAAGCACGACGACGACAAG<br>AUCAUCGACUACAAGGACGACGACGACAAGAUCAUCGAC<br>UACAAGGACGACGACGACAAGAUAAUUGACUAUAAAGAC<br>GACGACGAUAAAGUACUGGACUAUAAAGACGACGACGAC<br>AAGAUCAUCGACUACAAGGACGACGACGACAAGAUCAUC<br>GACUACAAGGACGACGACGACAAGAUUAUAGACUACAAA<br>GACGACGA CGAUAAAUUCAACUGAAA | SEQ ID NO: 047 |

TABLE 7

| | Base Length (b) | Sequence | |
|---|---|---|---|
| 8× FLAG (3) RNA | 264 | GGGA GCCACC AUG GACUACAAGGACGACGACGACAAG<br>AUCAUCGACUACAAGGACGACGACGACAAGAUCAUCGAC<br>UACAAGGACGACGACGACAAGAUAAUUGACUAUAAAGAC<br>GACGACGAUAAAGUACUGGACUAUAAAGACGACGACGAC<br>AAGAUGAUCGACUACAAGGACGACGACGACAAGAUCAUG<br>GACUACAAGGACGACGACGACAAGAUUAUAGACUACAAA<br>GACGACGACGAUAAAUUCAACGGAAAGGAAGA | SEQ ID NO: 048 |
| 8× FLAG (3 stop) RNA | 264 | GGGA GCCACC AUG GACUACAAGGACGACGACGACAAG<br>AUCAUCGACUACAAGGACGACGACGACAAGAUCAUCGAC<br>UACAAGGACGACGACGACAAGAUAAUUGACUAUAAAGAC<br>GACGACGAUAAAGUACUGGACUAUAAAGACGACGACGAC<br>AAGAUCAUCGACUACAAGGACGACGACGACAAGAUCAUC<br>GACUACAAGGACGACGACGACAAGAUUAUAGACUACAAA<br>GACGACGA CGAUAAAUUCAACUGAUAGUAAGA | SEQ ID NO: 049 |

4 FLAG RNA (SEQ ID NO: 43), 8× FLAG RNA (SEQ ID NO: 44) and 12× FLAG RNA (SEQ ID NO: 45) were synthesized by respectively using 4× FLAG DNA (SEQ ID NO: 36), 8× FLAG DNA (SEQ ID NO: 37) and 12× FLAG DNA (SEQ ID NO: 38) as template. More specifically, synthesis was carried out using T7 RNA Polymerase (Takara Bio Inc.). Two tubes each of reaction liquid (reaction liquid volume: 1 mL) consisting of 40 mM Tris-HCl (pH 8.0), 8 mM MgCl$_2$, 2 mM spermidine, 5 mM DTT, 2 mM rNTP each (Toyobo Co., Ltd.), 20 mM GMP (Wako Pure Chemical Industries, Ltd.), 1 unit/μL of RNase Inhibitor (Toyobo Co., Ltd.), 2.5 units/μL of T7 RNA Polymerase and 10 ng/μL of template DNA were prepared followed by carrying out transcription reactions by incubating for 2 hours at 42° C. DNase (Promega Corp.) was subsequently added to a concentration of 0.025 units/μL to the reaction liquids having 8× FLAG DNA and 12× FLAG DNA as templates followed by incubating for 15 minutes at 37° C. and carrying out a decomposition reaction on the template DNA in the reaction liquids. Subsequently, an equal volume of a mixed liquid of TE-saturated phenol and chloroform (5:1) was added to each reaction liquid to extract nucleic acids followed by adding 3 M aqueous sodium acetate solution (pH 5.2) and isopropyl alcohol to recover RNA by alcohol precipitation, and isolating the transcription product in the form of linear RNA using denaturing PAGE (5% polyacrylamide, 7.5 M urea, 25% formamide, 1×TBE, thickness: 1 mm). Bands containing the target product were visualized by UV shadowing, followed by cutting out the bands, finely crushing and extracting with eluate (10 mM EDTA (pH 8.0)). After desalting the extract with the Sep-Pak® C18 Cartridge (Waters Corp.) filter cartridge, the extract was eluted with 50% acetonitrile and concentrated with a centrifugal evaporator followed by freeze-drying. RNA was desalted and recovered from the freeze-dried product by alcohol precipitation. The resulting RNA was dissolved in ultrapure water and suitably diluted followed by measurement of the UV absorption spectrum and calculation of yield (recovered amount of 4× FLAG RNA: 3.56 nmol, recovered amount of 8× FLAG RNA: 10.06 nmol, recovered amount of 12× FLAG RNA: 5.75 nmol).

8× FLAG (2) RNA (SEQ ID NO: 46), 8× FLAG (stop) RNA (SEQ ID NO: 47), 8× FLAG (3) RNA (SEQ ID NO: 48) and 8× FLAG (3 stop) RNA (SEQ ID NO: 49) were synthesized using the MEGAscript® T7 Kit (Ampion Corp) T' transcript kit by respectively using 8× FLAG (2) DNA, 8× FLAG (stop, 8× FLAG(3) DNA and 8× FLAG(3 stop) DNA as template. More specifically, 75 mM GMP and 5 ng/μL of template DNA were added to the reaction liquids according to the product manual to bring the reaction liquid volume to 400 μL (600 μL for the reaction liquid volume in the case of 8× FLAG (stop) RNA), and each reaction liquid was incubated for about 16 hours at 37° C. (6 hours in the case of 8× FLAG (3) RNA and 8× FLAG (3 stop) RNA) to carry out transcription reactions. Subsequently, TURBO DNase™ (DNase) provided with the aforementioned kit was added to the reaction liquids and a reaction for analyzing template DNA was carried out according to the product manual. Subsequently, an equal volume of a mixed liquid of TE-saturated phenol and chloroform (5:1) was added to each reaction liquid to extract nucleic acids followed by adding 3 M aqueous sodium acetate solution (pH 5.2) and isopropyl alcohol to recover RNA by alcohol precipitation, and isolating the transcription product in the form of linear RNA using denaturing PAGE (5% polyacrylamide, 7.5 M urea, 25% formamide, 1×TBE, thickness: 1 mm). Bands containing the target product were visualized by UV shadowing, followed by cutting out the bands, finely crushing and extracting with eluate (10 mM EDTA (pH 8.0)). The entire amount of the extract (¼ the entire amount of the extract in the case of 8× FLAG(3) RNA and 8× FLAG(3 stop) RNA) was desalted with 0.5 mL of Amicon Ultra (cutoff molecular weight: 3K) (Millipore Corp.) or Amicon Ultra 4 (cutoff molecular weight: 3K) (Millipore Corp.) followed by recovery of RNA. The remaining extract of the 8× FLAG(3) RNA and 8× FLAG(3 stop) RNA (¾ the entire amount of extract) was desalted with the Sep-Pak® C18 Cartridge (Waters Corp.) filter cartridge, eluted with 50% acetonitrile, concentrated with a centrifugal evaporator and freeze-dried followed by desalting and recovery of RNA from the freeze-dried product by alcohol precipitation. The resulting RNA was dissolved in ultrapure water and suitably diluted followed by measurement of the UV absorption spectrum and calculation of yield (recovered amount of 8× FLAG(2) RNA: 0.975 nmol, recovered amount of 8× FLAG(stop) RNA: 2.01 nmol, recovered amount of 8× FLAG(3) RNA: 1.56 nmol, recovered amount of 8× FLAG(3 stop) RNA: 2.34 nmol).

(4) Synthesis of Cyclization Products (Cyclic RNA) by Cyclization Reaction of Transcribed RNA 4× FLAG RNA cyclization product (cyclic RNA of 4× FLAG RNA) from 4× FLAG RNA (SEQ ID NO: 43) using Adaptor 1 (SEQ ID NO: 18), 8× FLAG RNA cyclization product from 8× FLAG RNA (SEQ ID NO: 44) using Adaptor 2 (SEQ ID NO: 19), 12× FLAG RNA cyclization product from 12× FLAG RNA (SEQ ID NO: 45) using Adaptor 3 (SEQ ID NO: 20), 8× FLAG(2) RNA cyclization product from 8× FLAG(2) RNA (SEQ ID NO: 46) using Adaptor 4 (SEQ ID NO: 29), 8× FLAG(stop) RNA cyclization product from 8× FLAG(stop) RNA (SEQ ID NO: 47) using Adaptor 5 (SEQ ID NO: 30), 8× FLAG(3) RNA cyclization product from 8× FLAG(3) RNA (SEQ ID NO: 48) using Adaptor 6 (SEQ ID NO: 33), and 8× FLAG(3 stop) RNA cyclization product from 8× FLAG(3 stop) RNA (SEQ ID NO: 49) using Adaptor 7 (SEQ ID NO: 34) were respectively synthesized by ligase reactions. The ligase reactions were carried out in reaction liquids containing 1 μM transcribed RNA, 5 μM DNA oligonucleotide (Adaptors 1 to 7), 0.0125 units/μL of T4 RNA Ligase 2 (New England Biolabs Inc.), 50 mM Tris-HCl (pH 7.5), 2 mM $MgCl_2$, 1 mM DTT and 0.4 mM ATP (reaction liquid volume: 800 μL (with the exception that reaction liquid volume in the case of 4× FLAG RNA was 3000 μL, that in the case of 8× FLAG RNA and 12× FLAG RNA was 5000 μL, that in the case of 8× FLAG(3) RNA was 600 μL and that in the case of 8× FLAG(3 stop) RNA was 1000 μL).

More specifically, after heating the reaction liquid to which all components had been added except for the T4 RNA Ligase 2 for 3 minutes at 90° C., the reaction liquid was allowed to slowly cool to room temperature. Subsequently, the T4 DNA Ligase 2 was added to the reaction liquid followed by incubating for about 3 hours at 37° C. (about 16 hours in the case of the reaction liquids containing 8× FLAG(2) RNA and 8× FLAG(2 stop) RNA). After adding aqueous sodium acetate solution, aqueous glycogen solution and isopropyl alcohol to the reaction liquid and cooling, the RNA was precipitated and extracted followed by isolation of the cyclization products (cyclic RNA) using denaturing PAGE (5% polyacrylamide, 7.5 M urea, 25% formamide, 1×TBE, thickness: 1 mm). As a result of staining with SYBR® Green II (Takara Bio Inc.) stain after subjecting the reaction liquids to denaturing PAGE, cyclization products were confirmed to have been formed in each of the cyclization reaction liquids.

Figure 8:
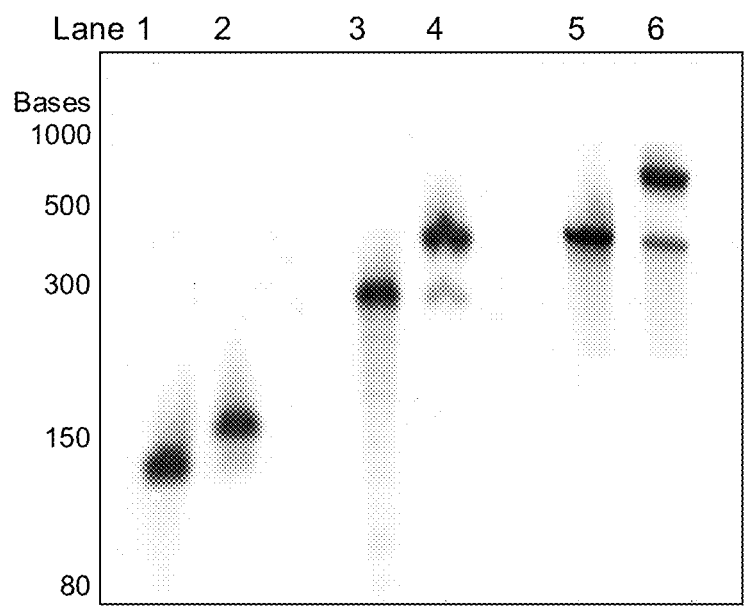
FIG. 8 is a stained image obtained by staining nucleic acids following electrophoresis of a cyclization product following purification in Example 2.
Figure 9:
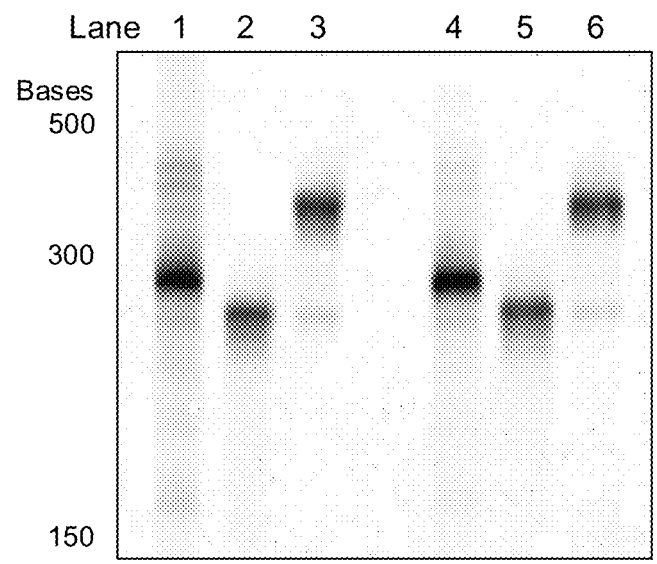
FIG. 9 is a stained image obtained by staining nucleic acids following electrophoresis of a cyclization product following purification in Example 2.
Figure 10:
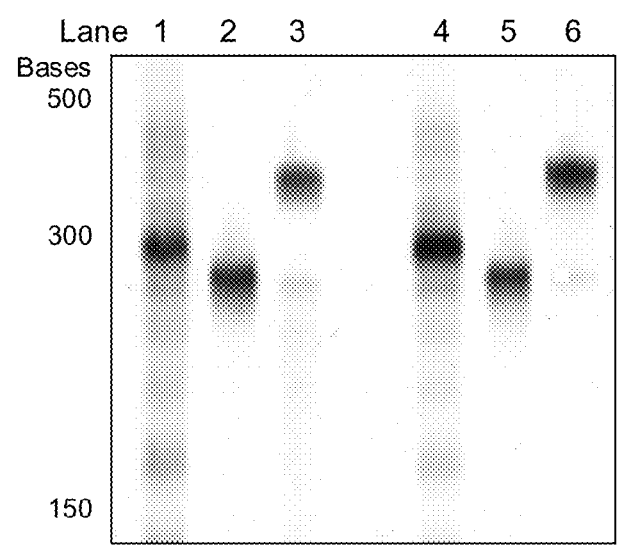
FIG. 10 is a stained image obtained by staining nucleic acids following electrophoresis of a cyclization product following purification in Example 2.

Bands containing the target products were visualized by UV shadowing, followed by cutting out the bands, finely crushing and extracting with eluate (10 mM EDTA (pH 8.0)). After desalting and concentrating the extracts with 0.5 mL of Amicon® Ultra (cutoff molecular weight: 3 K) (Millipore Corp.) or Amicon® Ultra 4 (cutoff molecular weight: 3 K) (Millipore Corp.) filter, RNA was desalted and recovered by alcohol precipitation. In the case of the reaction liquids of 4× FLAG RNA, 8× FLAG RNA and 12× FLAG RNA, after desalting and concentrating using a 0.5 mL Amicon® Ultra filter, the extracts were further desalted and concentrated using Microcron® Ultracel YM-10 (cutoff molecular weight: 10 K) filter followed by recovering the RNA by alcohol precipitation. The resulting RNA was dissolved in ultrapure water and suitably diluted followed by measurement of the UV absorption spectrum and calculation of yield (recovered amount of 4× FLAG RNA cyclization product: 375 pmol (yield: 12.5%), recovered amount of 8× FLAG RNA cyclization product: 396 pmol (yield: 7.93%), recovered amount of 12× FLAG RNA cyclization product: 253 pmol (yield: 5.05%), recovered amount of 8× FLAG (2) RNA cyclization product: 69.99 pmol (yield: 8.75%), recovered amount of 8× FLAG (stop) RNA cyclization product: 56.71 pmol (yield: 7.09%), recovered amount of 8× FLAG (3) RNA cyclization product: 35.56 pmol (yield: 5.93%), recovered amount of 8× FLAG(3 stop) RNA cyclization product: 84.82 pmol (yield: 8.48%)). Stained images obtained as a result of electrophoresing each of the purified cyclization products by denaturing PAGE and staining with SYBR® Green II (Takara Bio Inc.) stain are shown in FIGS. 8 to 10. In FIG. 8, 4× FLAG RNA was applied to Lane 1, 4× FLAG RNA cyclization product was applied to Lane 2, 8× FLAG RNA was applied to Lane 3, 8× FLAG cyclization product was applied to Lane 4, 12× FLAG RNA was applied to Lane 5, and 12× FLAG cyclization product was applied to Lane 6. In FIG. 9, 8× FLAG (2) DNA was applied to Lane 1, 8× FLAG (2) RNA was applied to Lane 2, 8× FLAG (2) RNA cyclization product was applied to Lane 3, 8× FLAG (stop) DNA was applied to Lane 4, 8× FLAG (stop) RNA was applied to Lane 5, and 8× FLAG (stop) RNA cyclization product was applied to Lane 6. In FIG. 10, 8× FLAG (3) DNA was applied to Lane 1, 8× FLAG (3) RNA was applied to Lane 2, 8× FLAG (3) RNA cyclization product was applied to Lane 3, 8× FLAG(3 stop) DNA was applied to Lane 4, 8× FLAG(3 stop) RNA was applied to Lane 5, and 8× FLAG(3 stop) RNA cyclization product was applied to Lane 6.

<Protein Synthesis Using RNA Cyclization Products (CyclicRNA) as Templates>

(5) Translation Reactions Using Rabbit Reticulocyte Extract

After heating 1.843 μM RNA cyclization product or 1.843 μM linear transcribed RNA prior to cyclization for 3 minutes at 65° C. followed by rapidly cooling with ice water, translation reactions were carried out by adding to rabbit reticulocyte extract. More specifically, reaction liquids (reaction liquid volume: 25 μL) were prepared consisting of 479.2 nM rapidly cooled RNA, 70% Rabbit Reticulocyte Lysate (Promega Corp.), 10 μM Amino Acid Mixture Minus Methionine, 10 μM Amino Acid Mixture Minus Leucine (both provided with the Rabbit Reticulocyte Lysate System (Promega Corp.)) and 0.8 units/μL of RNase Inhibitor (Toyobo Co., Ltd.), and translation reactions were carried out by incubating each reaction liquid for 1.5 hours to 19 hours at 30° C. Subsequently, 2.5 μL aliquots were sampled from the reaction liquids and mixed with 5 μL of 2×SDS sample buffer (0.125 M Tris-HCl (pH 8.0), 2% SDS, 30% glycerol, 0.02% bromophenol blue, 5% 2-mercaptoethanol), and after heating for 15 minutes at 70° C., the reaction liquids were electrophoresed using 5% polyacrylamide gel or 10% to 20% gradient polyacrylamide gel (Atto Corp.) (phoresis buffer: 25 mM Tris-HCl, 0.1% SDS, 192 mM glycine). After transferring the protein that developed in the gel onto a PVDF membrane (Millipore Corp.), the protein was reacted with mouse-produced anti-FLAG antibody and anti-mouse IgG antibody-peroxidase (HRP) complex (both available from Sigma-Aldrich Corp.) and bands specific to FLAG sequence were visualized (Light-Capture, Atto Corp.) using HRP substrate (SuperSignal® chemiluminescent substrate do the detection Western blot analysis, West Femto Maximum Sensitivity Substrate, Thermo Inc.). FIGS. 11 to 14 show the results of visualizing proteins containing FLAG. The reaction liquids described in Tables 8 to 11 were applied to each of the lanes in FIGS. 11 to 14.

TABLE 8

FIG. 11 5% SDS-PAGE

| | Reaction liquid template | Translation reaction time |
|---|---|---|
| Lane 1 | No RNA | 4 hours |
| Lane 2 | 4× FLAG RNA | 4 hours |
| Lane 3 | 4× FLAG RNA cyclization product | 4 hours |
| Lane 4 | 8× FLAG RNA | 4 hours |
| Lane 5 | 8× FLAG RNA cyclization product | 4 hours |
| Lane 6 | 12× FLAG RNA | 4 hours |
| Lane 7 | 12× FLAG RNA cyclization product | 4 hours |

TABLE 9

FIG. 12 5% SDS-PAGE

| | Reaction liquid template | Translation reaction time |
|---|---|---|
| Lane 1 | 8× FLAG RNA | 1.5 hours |
| Lane 2 | 8× FLAG RNA cyclization product | 1.5 hours |
| Lane 3 | 8× FLAG RNA | 4.5 hours |
| Lane 4 | 8× FLAG RNA cyclization product | 4.5 hours |
| Lane 5 | 8× FLAG RNA | 19 hours |
| Lane 6 | 8× FLAG RNA cyclization product | 18 hours |

TABLE 10

FIG. 13 10%-20% SDS-PAGE

| | Reaction liquid template | Translation reaction time |
|---|---|---|
| Lane 1 | No RNA | 16 hours |
| Lane 2 | 8× FLAG RNA | 16 hours |
| Lane 3 | 8× FLAG RNA cyclization product | 16 hours |
| Lane 4 | 8× FLAG(2) RNA | 16 hours |
| Lane 5 | 8× FLAG(2) RNA cyclization product | 16 hours |
| Lane 6 | 8× FLAG(stop) RNA | 16 hours |
| Lane 7 | 8× FLAG(stop) RNA cyclization product | 16 hours |

TABLE 11

FIG. 14 10%-20% SDS-PAGE

| | Reaction liquid template | Translation reaction time |
|---|---|---|
| Lane 1 | No RNA | 16 hours |
| Lane 2 | 8× FLAG(3) RNA | 16 hours |
| Lane 3 | 8× FLAG(3) RNA cyclization product | 16 hours |
| Lane 4 | 8× FLAG(3 stop) RNA | 16 hours |
| Lane 5 | 8× FLAG(3 stop) RNA cyclization product | 16 hours |

Figure 11:
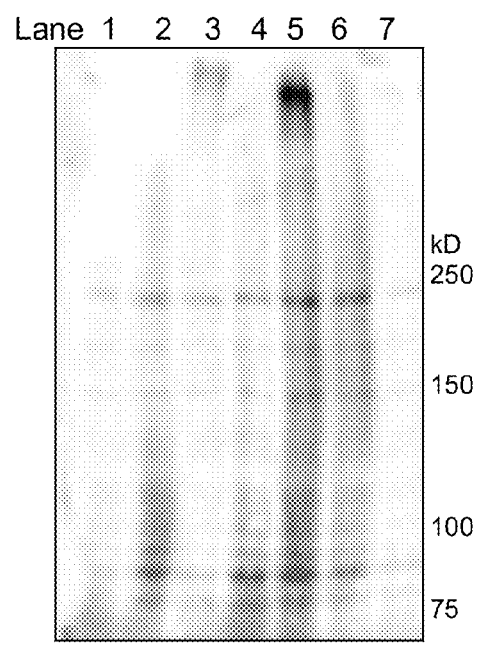
FIG. 11 is a stained image of protein bands containing FLAG obtained as a result of electrophoresis of a reaction liquid of a cell-free translation reaction in Example 2.
Figure 12:
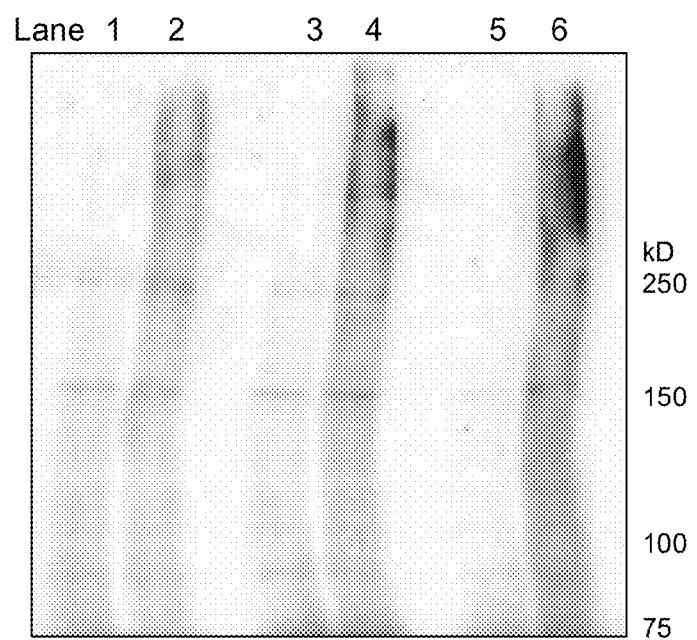
FIG. 12 is a stained image of protein bands containing FLAG obtained as a result of electrophoresis of a reaction liquid of a cell-free translation reaction in Example 2.
Figure 13:
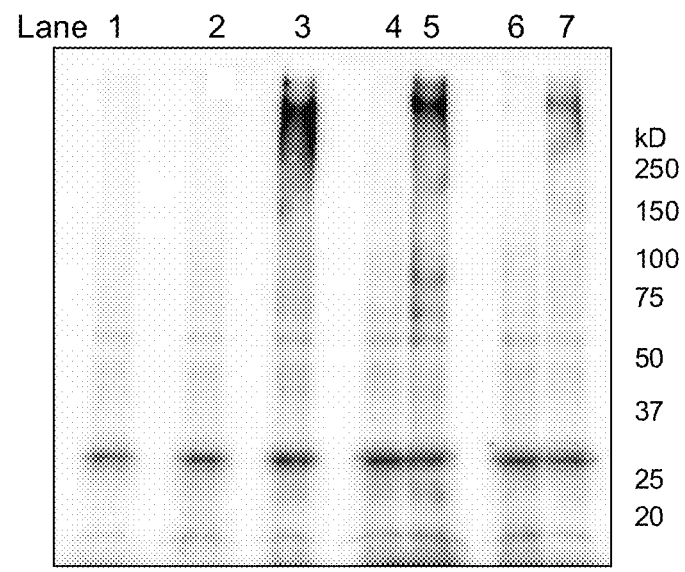
FIG. 13 is a stained image of protein bands containing FLAG obtained as a result of electrophoresis of a reaction liquid of a cell-free translation reaction in Example 2.
Figure 14:
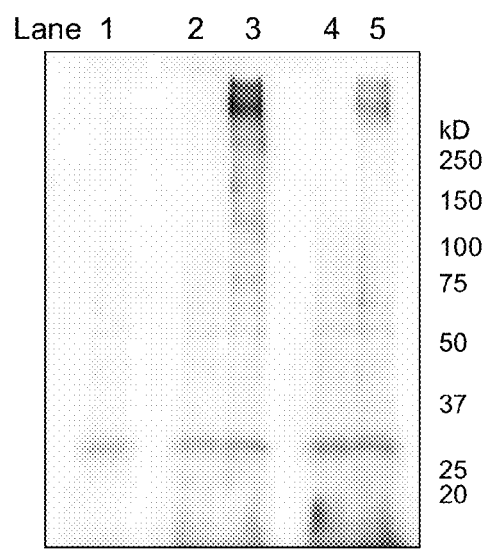
FIG. 14 is a stained image of protein bands containing FLAG obtained as a result of electrophoresis of a reaction liquid of a cell-free translation reaction in Example 2.

As a result, as shown in FIG. 11, high molecular weight translation products (protein repeats) were detected in the case of using 4× FLAG RNA cyclization product as template (Lane 3) and in the case of using 8× FLAG RNA cyclization product (Lane 5) as template. In particular, the largest number of protein repeats was synthesized in the case of using 8× FLAG RNA cyclization product as template. In addition, as shown in FIG. 12, a larger number of high molecular weight translation products (protein repeats) were detected the longer the duration of the translation reaction. In addition, as shown in FIGS. 13 and 14, high molecular weight translation products were also detected, although in smaller amounts, even in the case of the 8× FLAG(stop) RNA cyclization product and 8× FLAG(3 stop) RNA cyclization product having a stop codon or stop codons.

Example 3

Protein was synthesized in a human-derived cell-free system using the RNA cyclization products synthesized in Example 2 and linear transcribed RNA prior to cyclization as templates.

Translation reactions were carried out according to the product manual using the AvidExpress™ Cell-Free Translation System (derived from human HeLaS3 cells, Avidity Inc.) to a final RNA template concentration of 1.2 μM. Following completion of the reactions, 2.5 μL aliquots were sampled from each reaction liquid and electrophoresed using 10% to 20% gradient polyacrylamide gel in the same manner as Example 2, and after transferring the protein that developed in the gel to a PVDF membrane, the protein was reacted with anti-FLAG antibody and anti-mouse IgG antibody-HRP complex followed by reacting with HRP substrate to visualize protein bands specific to the FLAG sequence.

Figure 15:
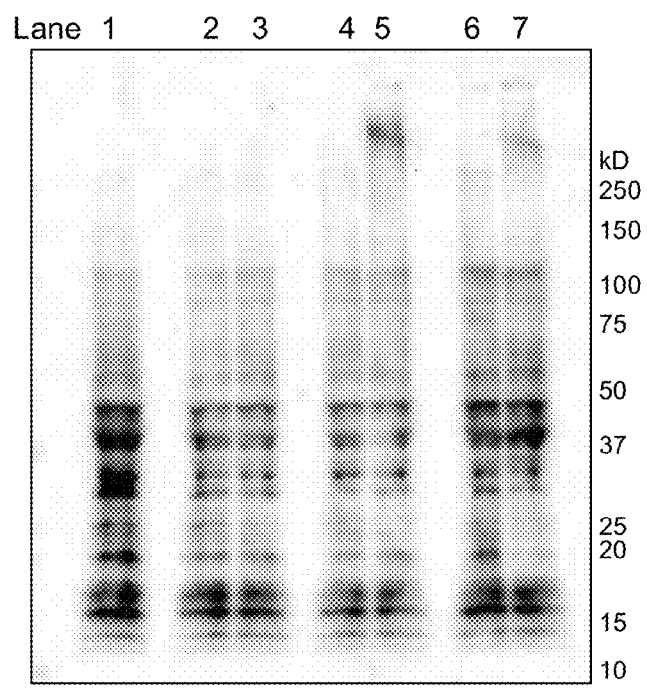
FIG. 15 is a stained image of protein bands containing FLAG obtained as a result of electrophoresis of a reaction liquid of a cell-free translation reaction in Example 3.

FIG. 15 shows the results of visualizing protein bands containing FLAG. In FIG. 15, RNA-free reaction liquid was applied to Lane 1, reaction liquid containing 4× FLAG RNA was applied to Lane 2, reaction liquid containing 4× FLAG RNA cyclization product was applied to Lane 3, reaction liquid containing 8× FLAG RNA was applied to Lane 4, reaction liquid containing 8× FLAG RNA cyclization product was applied to Lane 5, reaction liquid containing 12× FLAG RNA was applied to Lane 6, and reaction liquid containing 12× FLAG RNA cyclization product was applied to Lane 7. As shown in FIG. 15, high molecular weight translation products (protein repeats) were detected in the case of using 8× FLAG RNA cyclization product as template (Lane 5) and using 12× FLAG RNA cyclization product as template (Lane 7). In particular, the largest number of protein repeats was synthesized in the case of using the 8× FLAG RNA cyclization product as template.

Example 4

Protein was synthesized using a human intracellular translation system by using the RNA cyclization products synthesized in Example 2 and linear transcribed RNA prior to cyclization as templates.

First, 145 µL of Opti-MEM® I Reduced-Serum Medium (Invitrogen Corp.) and 5 µL of 2.4 µM template RNA solution were mixed in each well of a 12-well cell culturing plate (Becton, Dickinson and Co.) followed by the addition of 2 µL of Lipofectamine® RNA iMAX (Invitrogen Corp.) transfection reagent, mixing and allowing to stand undisturbed for 15 minutes. Subsequently, 850 µL of HeLa cells (cultured cell line derived from human cervical cancer, provided by the Riken Bioresource Center) diluted to 100,000 cells per 1 mL using Dulbecco's Modified Eagle Medium (Wako Pure Chemical Industries, Ltd.) containing 10% fetal bovine serum (Invitrogen Corp.) were added followed by culturing for 24 hours at 37° C. in a 5% $CO_2$ environment (RNA final concentration: 12 nM). After lysing the cells by adding 200 µL of cell lysing buffer (CST Japan K.K.) per well, the lysed cells were subjected to centrifugal separation treatment. 7.5 µL of the resulting supernatant was sampled and electrophoresed using 10% to 20% gradient polyacrylamide gel in the same manner as Example 2, and protein that developed in the gel was transferred to a PVDF membrane. Subsequently, the protein was reacted with anti-FLAG antibody or anti-actin antibody (Santa Cruz Biotechnology Inc.) and anti-mouse IgG antibody-HRP complex followed by reacting with HRP substrate to visualize bands of protein specific to the FLAG sequence or bands of actin protein.

Figure 16:
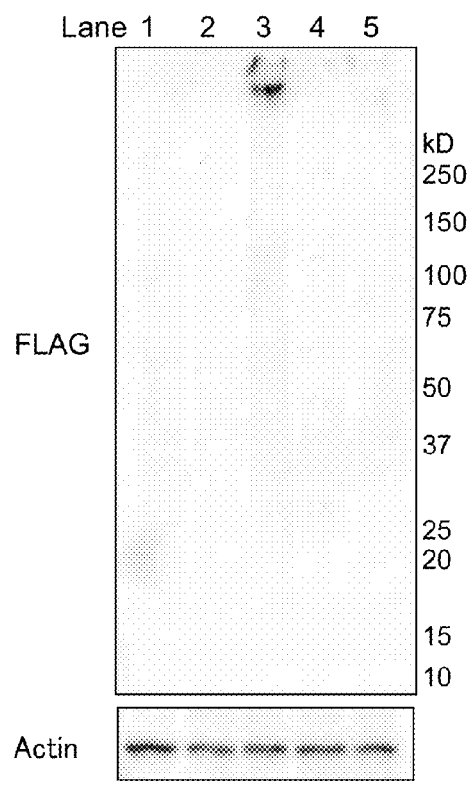
FIG. 16 is a stained image of protein bands containing FLAG and actin protein bands obtained as a result of electrophoresis of reaction liquids of a cell-free translation reaction in Example 4.

FIG. 16 shows the results of visualizing bands of protein containing FLAG and actin protein bands. In FIG. 16, an RNA-free reaction liquid was applied to Lane 1, a reaction liquid containing 8× FLAG (2) RNA was applied to Lane 2, a reaction liquid containing 8× FLAG(2) RNA cyclization product was applied to Lane 3, a reaction liquid containing 8× FLAG(stop) RNA was applied to Lane 4, and a reaction liquid containing 8× FLAG(stop) RNA cyclization product was applied to Lane 5. As shown in FIG. 16, a high molecular weight translation product (protein repeat) was detected in the case of using the 8× FLAG(2) RNA cyclization product as template (Lane 3). In addition, since actin protein bands were present in all lanes at about the same density, the amount of protein present in the cell lysates added to each reaction liquid were indicated to be nearly equal.

According to the present example, rotary protein translation was demonstrated to be able to be carried out by introducing the cyclic RNA for eukaryotic cells of the present invention into mammalian cells.

Example 5

Protein was synthesized using a human intracellular translation system by using the RNA cyclization products synthesized in Example 2 and linear transcribed RNA prior to cyclization as templates.

First, 45 µL of Opti-MEM® I Reduced-Serum Medium (Invitrogen Corp.) and 4 µL of 2 µM template RNA solution were mixed in each well of a 24-well cell culturing plate (Becton, Dickinson and Co.) followed by the addition of 1 µL of Lipofectamine® RNA iMAX (Invitrogen Corp.) transfection reagent, mixing and allowing to stand undisturbed for 15 minutes. Subsequently, 350 µL of HeLa cells diluted to 143,000 cells per 1 mL using Dulbecco's Modified Eagle Medium (Wako Pure Chemical Industries, Ltd.) containing 10% fetal bovine serum were added followed by culturing for 24 hours at 37° C. in a 5% $CO_2$ environment (RNA final concentration: 20 nM). After lysing the cells by adding 30 µL of cell lysing buffer (CST Japan K.K.) per well, the lysed cells were subjected to centrifugal separation treatment. The amount of protein in the resulting supernatant was measured using Coomassie Plus (Thermo Fisher Scientific, Inc.) and the protein concentration was adjusted to 1.5 mg/mL using cell lysing buffer. After adjusting the protein concentration, 7.5 µL of the supernatant was sampled and electrophoresed using 10% to 20% gradient polyacrylamide gel in the same manner as Example 2, and protein that developed in the gel was transferred to a PVDF membrane. Subsequently, the protein was reacted with anti-FLAG antibody or anti-actin antibody (Santa Cruz Biotechnology Inc.) and anti-mouse IgG antibody-HRP complex followed by reacting with HRP substrate to visualize bands of protein specific to the FLAG sequence or bands of actin protein (ChemiDoc XRS Plus, Bio-Rad Laboratories, Inc.).

Figure 17:
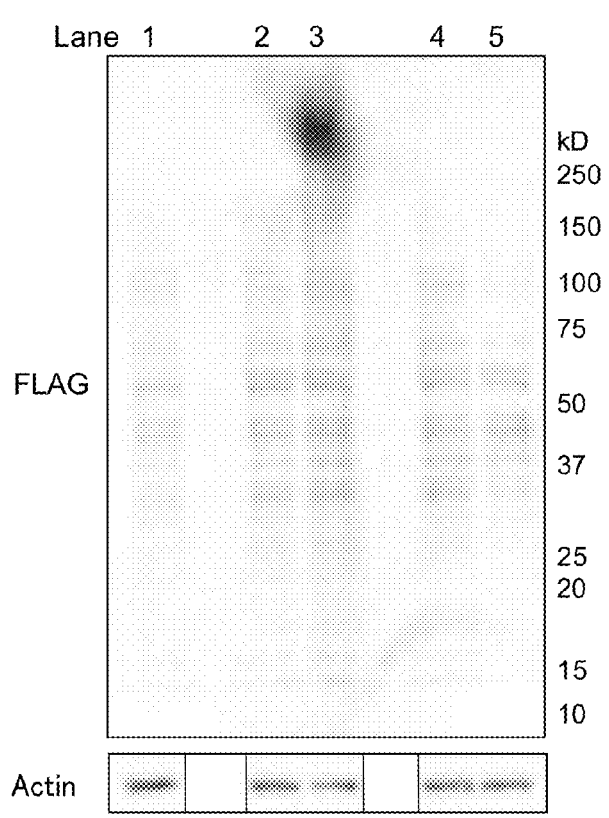
FIG. 17 is a stained image of protein bands containing FLAG and actin protein bands obtained as a result of electrophoresis of reaction liquids of a cell-free translation reaction in Example 5.

FIG. 17 shows the results of visualizing bands of protein containing FLAG and actin protein bands. In FIG. 17, an RNA-free reaction liquid was applied to Lane 1, a reaction liquid containing 8× FLAG (3) RNA was applied to Lane 2, a reaction liquid containing 8× FLAG (3) RNA cyclization product was applied to Lane 3, a reaction liquid containing 8× FLAG (3 stop) RNA was applied to Lane 4, and a reaction liquid containing 8× FLAG (3 stop) RNA cyclization product was applied to Lane 5. As shown in FIG. 17, a high molecular weight translation product (protein repeat) was detected in the case of using the 8× FLAG (3) RNA cyclization product as template (Lane 3). In addition, since actin protein bands were present in all lanes at about the same density, the amount of protein present in the cell lysates added to each reaction liquid were indicated to be nearly equal.

Example 6

RNA translation products introduced into cells were detected by transfecting HeLa cells with cyclic RNA of 8× FLAG RNA synthesized in section (4) of Example 2 and staining the cells using fluorescently labeled anti-FLAG antibody.

First, 500 µL of HeLa cells diluted to 100,000 cells per mL using Dulbecco's Modified Eagle Medium (Wako Pure Chemical Industries, Ltd.) containing 10% fetal bovine serum were added to each well of a 24-well cell culturing plate having a cover glass placed in each well (Becton, Dickinson and Co.) followed by culturing overnight at 37° C. in a 5% $CO_2$ environment. Subsequently, after removing the medium from each well, 200 µL of Opti-MEM® I Reduced-Serum Medium (Invitrogen Corp.) were added. 32.5 µL of Opti-MEM® I Reduced-Serum Medium (Invitrogen Corp.) and 2.5 µL of 2 µg/mL template RNA solution were mixed followed by the addition of a solution obtained by mixing 12 µL of Opti-MEM® I Reduced-Serum Medium (Invitrogen Corp.) and 3 µL of Oligofectamine™ (Invitrogen Corp.) transfection reagent to this solution, allowing to stand undisturbed for 15 minutes, adding to each well and culturing for 6 hours at 37° C. in a 5% $CO_2$ environment.

The medium was removed at 6 hours after transfection and 500 μL, of Dulbecco's Modified Eagle Medium (Wako Pure Chemical Industries, Ltd.) containing 10% fetal bovine serum were added to each well followed by further culturing for 24 hours at 37° C. in a 5% $CO_2$ environment. Subsequently, after removing the medium and washing, the cells were fixed with 4% PFA/PBS. After treating the cells with 0.3% Triton® X-100 (polyethylene oxide non-ionic surfactant)/PBS and blocking with 1% BSA/PBS, mouse anti-FLAG antibody (Sigma-Aldrich Japan K.K.) prepared with 1% BSA/PBS was added followed by incubating for 1 hour. After washing, Alexa Fluor® 488-labeled anti-mouse IgG antibody (Life Technologies Japan K.K.) dye prepared with 1% BSA/PBS was added followed by incubating for 1 hour. After washing, the cells were observed microscopically. The results are shown in FIGS. 18 and 19.

Figure 18:
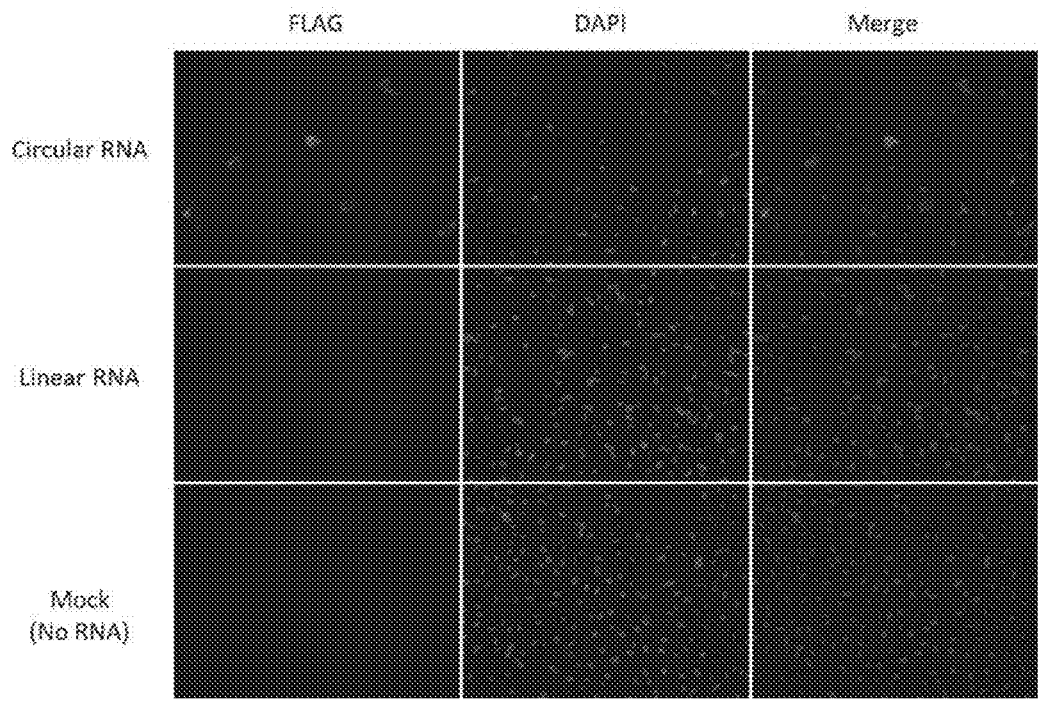
FIG. 18 shows the results of carrying out observations with a fluorescence microscope using a 10× object lens in Example 6.
Figure 19:
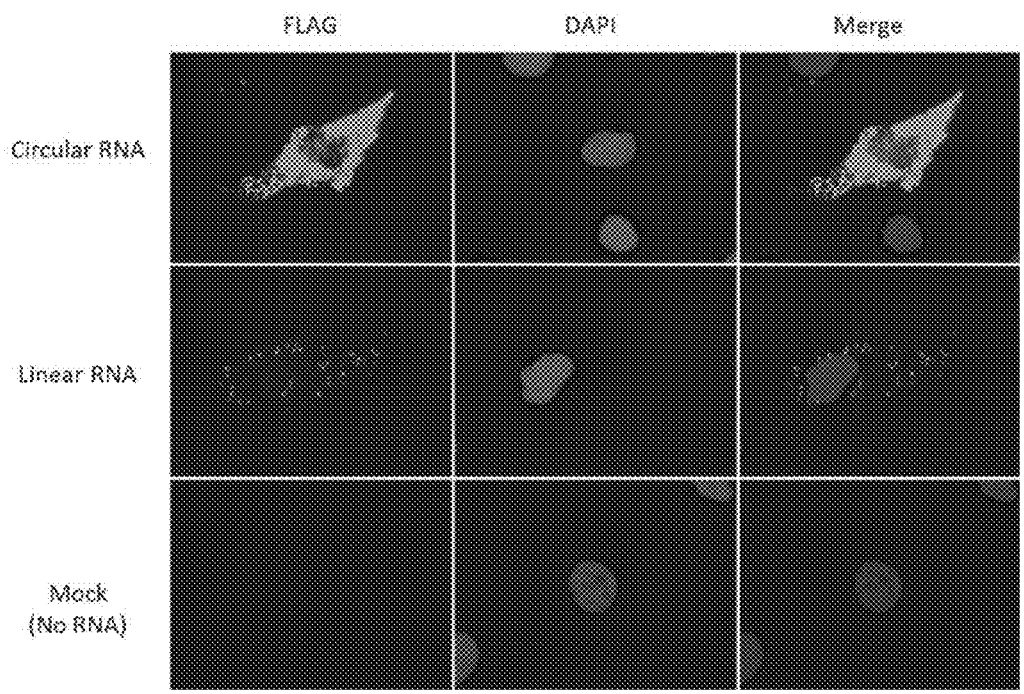
FIG. 19 shows the results of carrying out observations with a fluorescence microscope using a 60× object lens in Example 6.

According to the results shown in FIGS. 18 and 19, fluorescence attributable to cyclic RNA was determined to be widely distributed throughout the cells, while fluorescence attributable to linear RNA was only detected in the form of small dots. In addition, fluorescence was not observed for the control in which there was no RNA (mock).

INDUSTRIAL APPLICABILITY

According to the cyclic RNA and protein production method using that cyclic RNA of the present invention, since protein repeats can be easily synthesized in not only cell-free systems but also within cells, the present invention can be preferably used in not only research and other academic fields, but in manufacturing fields such as the manufacturing of pharmaceuticals, foods, beverages, cosmetics or chemicals that utilizes peptides and proteins.

The invention claimed is:

1. A method for producing protein in eukaryotic cells or in a eukaryotic cell expression system, comprising:
    introducing a cyclic RNA into eukaryotic cells, or adding the cyclic RNA to a eukaryotic cell-free expression system; and
    expressing a protein encoded by the cyclic RNA using the cyclic RNA in the eukaryotic cells or eukaryotic cell-free expression system,
    wherein the cyclic RNA encodes a protein, has a full-length number of bases that is equal to or greater than 102, and is a multiple of 3, has at least one start codon, does not have a stop codon in the same reading frame as the start codon, and does not contain an internal ribosome entry site (IRES).

2. The method for producing protein according to claim 1, wherein the eukaryotic cells are mammalian cells, and the eukaryotic cell-free expression system is a mammalian cell-free expression system.

3. A method for producing protein in a prokaryotic cell or in a prokaryotic cell expression system, comprising:
    introducing a cyclic RNA into prokaryotic cells, or adding the cyclic RNA to a prokaryotic cell-free expression system; and
    expressing a protein encoded by the cyclic RNA using the cyclic RNA in the prokaryotic cells or the prokaryotic cell-free expression system,
    wherein the cyclic RNA encodes a protein, has a full-length number of bases that is from 102 to 561 and is a multiple of 3, has at least one ribosome binding site recognized by ribosomes derived from prokaryotic cells, has a plurality of start codons, with only one of the plurality of start codons within 1 to 20 bases downstream from the ribosome binding site, and does not have a stop codon in the same reading frame as the start codon.

4. The method according to claim 3, wherein the cyclic RNA does not contain an internal ribosome entry site (IRES).

5. The method according to claim 3, wherein the cyclic RNA has an Shine-Dalgarno (SD) sequence as the ribosome binding site.

6. The method according to claim 3, wherein the cyclic RNA has an open reading frame comprising the start codon within 1 to 20 bases downstream from the ribosome binding site, and has no other reading frame which comprises a start codon.

7. The method according to claim 3, wherein the cyclic RNA comprises a stop codon in a different reading frame from the start codon.

8. The method according to claim 3, wherein the protein comprises long chain repeated regions of peptide sequences defined by the cyclic RNA.

9. The method according to claim 3, wherein the cyclic RNA comprises a domain encoding a protease cleavage site.

10. The method according to claim 1, wherein the cyclic RNA has a Kozak sequence upstream from the start codon.

11. The method according to claim 1, wherein the cyclic RNA has an open reading frame comprising the start codon, and has no other reading frame which comprises a start codon.

12. The method according to claim 1, wherein the cyclic RNA comprises a stop codon in a different reading frame from the start codon.

13. The method according to claim 1, wherein the protein comprises long chain repeated regions of peptide sequences defined by the cyclic RNA.

14. The method according to claim 1, wherein the cyclic RNA comprises a domain encoding a protease cleavage site.

15. The method according to claim 1, wherein the cyclic RNA comprises a full-length number of bases that is less than or equal to 561 bases.

* * * * *